(12) United States Patent
Kato et al.

(10) Patent No.: US 11,197,991 B2
(45) Date of Patent: Dec. 14, 2021

(54) GEL SHEET

(71) Applicant: SEKISUI PLASTICS CO., LTD., Osaka (JP)

(72) Inventors: Kazuki Kato, Ibaraki (JP); Ryo Iizuka, Ibaraki (JP); Takaaki Hatori, Ibaraki (JP); Takashi Motomura, Shiga (JP); Kazuhiro Yoshikawa, Tokyo (JP); Yoshiki Nakayama, Tokyo (JP)

(73) Assignee: SEKISUI PLASTICS CO., LTD., Osaka (JP)

( * ) Notice: Subject to any disclaimer, the term of this patent is extended or adjusted under 35 U.S.C. 154(b) by 155 days.

(21) Appl. No.: 16/313,078

(22) PCT Filed: Jun. 27, 2017

(86) PCT No.: PCT/JP2017/023537
§ 371 (c)(1),
(2) Date: Dec. 24, 2018

(87) PCT Pub. No.: WO2018/003787
PCT Pub. Date: Jan. 4, 2018

(65) Prior Publication Data
US 2019/0217079 A1    Jul. 18, 2019

(30) Foreign Application Priority Data

Jun. 27, 2016    (JP) ............................. JP2016-126983
Sep. 30, 2016    (JP) ............................. JP2016-193371

(51) Int. Cl.
*A61N 1/04*    (2006.01)

(52) U.S. Cl.
CPC ............. *A61N 1/0496* (2013.01); *A61N 1/04* (2013.01)

(58) Field of Classification Search
CPC ................................ A61N 1/04; A61N 1/0496
See application file for complete search history.

(56) References Cited

U.S. PATENT DOCUMENTS

| | | | | |
|---|---|---|---|---|
| 4,002,221 A | * | 1/1977 | Buchalter | A61B 5/411 181/0.5 |
| 5,069,908 A | * | 12/1991 | Henley | A61K 9/0009 424/449 |

(Continued)

FOREIGN PATENT DOCUMENTS

| | | |
|---|---|---|
| EP | 1 052 933 A2 | 11/2000 |
| JP | H11-235387 A | 8/1999 |

(Continued)

OTHER PUBLICATIONS

ISR in PCT/JP2017/023537, dated Sep. 12, 2017.

(Continued)

*Primary Examiner* — Eric D. Bertram
(74) *Attorney, Agent, or Firm* — Greenblum & Bernstein, P.L.C.

(57) ABSTRACT

An object of the present invention is to provide a gel sheet comprising an intermediate base, having no variation in adhesiveness.
A gel sheet 1 comprising a gel material 10 and an intermediate base 20 embedded in the gel material 10, wherein when T represents the thickness of the gel sheet 1, and S represents the amplitude of the intermediate base 20, a relation represented by the following expression (1) is satisfied:

$S/T \leq 0.4$    (1)

10 Claims, 9 Drawing Sheets

(56) References Cited

U.S. PATENT DOCUMENTS

| | | | | |
|---|---|---|---|---|
| 5,868,136 | A | * | 2/1999 | Fox ............... A61N 1/0496 252/500 |
| 6,038,464 | A | * | 3/2000 | Axelgaard ........ A61B 5/04087 600/391 |
| 7,540,979 | B2 | * | 6/2009 | Perrault ............. C08F 283/06 252/500 |
| 8,548,557 | B2 | * | 10/2013 | Garstka ........... A61B 5/04087 600/391 |
| 9,211,400 | B2 | | 12/2015 | Bachinski et al. |
| 9,481,771 | B2 | * | 11/2016 | Tamesue ................ C09J 5/00 |
| 2007/0088332 | A1 | | 4/2007 | Akiyama et al. |
| 2011/0319975 | A1 | * | 12/2011 | Ho ..................... A61N 1/0496 607/139 |
| 2012/0041296 | A1 | | 2/2012 | Garstka et al. |
| 2015/0025479 | A1 | * | 1/2015 | Davis .................. A61P 17/00 604/290 |

FOREIGN PATENT DOCUMENTS

| | | |
|---|---|---|
| JP | 2002-501804 A | 1/2002 |
| JP | 2003268336 | 9/2003 |
| JP | 2007085461 | 4/2007 |
| JP | 2007-202835 A | 8/2007 |
| JP | 2013-074990 A | 4/2013 |
| JP | 2013-202194 A | 10/2013 |
| JP | 2013-202336 A | 10/2013 |
| JP | 2014-522700 | 9/2014 |
| JP | 5815019 | 10/2015 |
| JP | 5844594 B2 | 1/2016 |
| JP | 2016067653 A | 5/2016 |
| WO | WO 2012/124216 A1 | 9/2012 |
| WO | 2016/027383 A1 | 2/2016 |

OTHER PUBLICATIONS

JP Office Action issued in JP App. No. 2016-126983 dated Jul. 16, 2019.
EESR for EP App. No. 17 82 0141.4 dated Feb. 28, 2020.
Korean Office Action, Korean Patent Office, Application No. 10-2019-7000170, dated May 21, 2020.
Notice of Allowance in corresponding Korean Application No. 10-2019-7000170, dated Nov. 20, 2020.
Office Action in corresponding Japanese Application No. 2019-182576, dated Nov. 10, 2020.

* cited by examiner

A

B

A

B

A

B

A

B

ID SHEET

TECHNICAL FIELD

The present invention relates to a gel sheet.

BACKGROUND ART

Gel sheets are suitably used as a surgical tape to be attached to a living body, a fixing tape of various medical equipment, a bioelectrode pad to be attached to a living body, an electrocardiogram electrode, and an industrial adhesive tape for building materials, electronic materials, etc., and the like. In many cases, an intermediate base is embedded in these gel sheets for the purpose of reinforcement and improvement of shape retention in cutting.

For example. Patent Literature 1 discloses a hydrogel comprising a carboxylic acid polymer as a component for forming a gel skeleton, a water-insoluble polyvalent metal as a crosslinking component, water and an alkali metal salt of ascorbyl palmitate phosphate, and it is described that the hydrogel can include an intermediate base from the perspective of imparting strength and the like. It is also described that besides a nonwoven fabric made of synthetic resin fiber such as polyester, a knit such as tricot and a sheet-like material such as woven fabric can be applied as the intermediate base.

Also, an adhesive hydrogel is suitably used as an adhesive hydrogel sheet to constitute a percutaneous absorption preparation, a cosmetic pack, or the like to be attached to a living body. Furthermore, a hydrogel containing an electrolyte such as inorganic salt can impart conductivity, so that the hydrogel can also be suitably used as an adhesive and conductive hydrogel sheet to constitute an electrode pad for use on a living body, for industrial measurement, or the like. An electrode pad for use on a living body having an adhesive and conductive hydrogel sheet is used in various medical equipment including measurement equipment for use on a living body for measuring bioelectricity such as electrocardiogram, and electrotherapeutic equipment for use on a living body that applies a voltage to a living body to obtain a therapeutic effect.

For example, in Patent Literature 2, an adhesive hydrogel comprising a polymer matrix in which a material for forming polymer matrix is polymerized, water, and a polyhydric alcohol, and an electrode pad made from the adhesive hydrogel are described.

Electrotherapeutic equipment for use on a living body for applying a current to a living body has been conventionally used to apply an alternating current or a pulsed current. In contrast, electrotherapeutic equipment for use on a living body for applying a direct current has been recently developed (Patent Literatures 3 and 4). It is considered that the activity of intracellular organelles such as cells or mitochondria in vivo can be efficiently activated by applying a direct current to a living body in comparison with applying an alternating current to a living body (Patent Literature 4).

CITATION LIST

Patent Literature

Patent Literature 1: WO 2012/124216 (Claim 1, 0046)
Patent Literature 2: JP Patent No. 5844594
Patent Literature 3: JP Patent Publication (Kokai) No. 11-235387A (1999)
Patent Literature 4: JP Patent Publication (Kokai) No. 2013-202194A

SUMMARY OF INVENTION

Technical Problem

An intermediate base of a conventional gel sheet is just present in the gel sheet, and the effect on the operability of the gel sheet in cutting and the like only has been focused. On the other hand, the gel sheet including a conventional intermediate base has a problem in that it has some variation in adhesiveness to the skin. The presence of variation in adhesiveness results in a problem of, for example, producing both pads having good adhesiveness, and pads having poor adhesive force and not adhering to the skin, for use as a gel pad of electrode.

In view of the above problem, an object of the present invention, therefore, is to provide a gel sheet comprising an intermediate base having no variation in adhesiveness.

Also, having both adhesiveness and conductivity, a gel sheet made of hydrogel is used as a component member of an electrode pad in various biological or industrial measurement equipment. In the case where a gel sheet is applied to an electrode pad in specific equipment, however, several problems have existed. For example, in equipment such as electrotherapeutic equipment for use on a living body, when a direct current is applied to an adherend for a certain time period using an electrode pad including a conventional gel sheet, electrolysis may occur in the internal part of the gel sheet. In this case, the pH of the gel sheet on the negative electrode side may increase along with generation of hydroxide ions. Also, on the positive electrode side of the gel sheet, bubbles occur along with generation of oxygen, so that conductivity may be reduced. For example, reduction in the content of an electrolyte such as an inorganic salt in the gel sheet to suppress the progress of electrolysis may reduce the conductivity of the gel sheet. On the other hand, an increase of the content of an inorganic salt in the gel sheet to improve the conductivity may accelerate the progress of electrolysis.

An object of the present invention, therefore, is to provide a gel sheet made of conductive hydrogel capable of substantially suppressing the increase in pH and/or the decrease in conductivity even when a direct current is applied for a certain time period.

Solution to Problem

As a result of extensive studies by the present inventors, it was found that the variation of the adhesiveness is caused by slight waving of an intermediate base in the internal part of the gel sheet and can be suppressed by controlling the extent of the waving within a specified range, so that the invention has been accomplished.

Further, the present inventors prepared a gel sheet of laminated conductive hydrogel having at least two gel sheet layers by alternately stacking two gel sheet layers made of hydrogel having a different inorganic salt content in a predetermined range. The present inventors found that when a direct current is applied, for a certain time period, to a gel sheet having such a construction with a gel sheet layer containing a large amount of inorganic salt disposed adjacent to the positive electrode, and with a gel sheet layer containing a smaller amount of inorganic salt than that contained in the gel sheet layer, and at least one acid, disposed adjacent to the negative electrode, the increase in pH and the decrease in conductivity were substantially suppressed. Based on the finding, the present inventors have accomplished the invention.

In other words, the gist of the present invention is as follows.

(1) A gel sheet comprising a gel material and an intermediate base embedded in the gel material, and satisfying the following expression (1):

$$S/T \leq 0.4 \tag{1}$$

wherein T represents a thickness of the gel sheet, and S represents an amplitude of the intermediate base.

(2) The gel sheet according to the above (1), satisfying the following expression (2):

$$S/T \leq 0.2 \tag{2}$$

(3) The gel sheet according to the above (1) or (2), wherein the gel material comprises at least two gel sheet layers having a gel sheet layer A and a gel sheet layer B alternately stacked.

(4) The gel sheet according to any one of the above (1) to (3), wherein the intermediate base is a membrane selected from the group consisting of a semipermeable membrane, an ion exchange membrane, a microfiltration membrane, an ultrafiltration membrane and a nanofiltration membrane.

(5) The gel sheet according to any one of the above (1) to (3), wherein the intermediate base is a nonwoven fabric.

(6) The gel sheet according to the above (3), wherein
the gel sheet layer A comprises at least one inorganic salt at a total content of X wt % relative to the total weight of the gel sheet layer A; and the gel sheet layer B comprises at least one inorganic salt at a total content of Y wt % relative to the total weight of the gel sheet layer B, wherein Y is less than X; and
the gel sheet layer B comprises at least one acid.

(7) The gel sheet according to the above (6), wherein the at least one acid comprises an organic acid.

(8) The gel sheet according to the above (6) or (7), wherein X and Y satisfy, the following expression (3):

$$0 \leq Y < X \leq 15 \tag{3}$$

(9) The gel sheet according to any one of the above (6) to (8), wherein when the gel sheet layer B has a water content of a wt % relative to the total weight of the gel sheet layer B, Y and α satisfy the following expression (4):

$$0 \leq Y/\alpha \leq 0.03 \tag{4}$$

(10) The gel sheet according to any one of the above (6) to (9), wherein when the gel sheet layer A has a thickness of a (mm), and the gel sheet layer B has a thickness of b (mm), a and b satisfy the following expressions (5) and (6):

$$b/a \geq 1 \tag{5}$$

$$0.6 \leq a+b \leq 3.0 \tag{6}$$

(11) An electrode pad comprising the gel sheet according to any one of the above (6) to (10) and an electrode electrically connected to the gel sheet layer A or the gel sheet layer B of the gel sheet.

(12) An electrode pad for use on a living body, comprising the gel sheet according to any one of the above (6) to (10) and an electrode electrically connected to the gel sheet layer A or the gel sheet layer B of the gel sheet, wherein the gel sheet layer A or the gel sheet layer B not connected to the electrode of the gel sheet is used as a part in contact with a living body.

(13) An electrotherapeutic equipment for use on a living body, comprising the electrode pad for use on a living body according to the above (12) and a power supply part electrically connected to the electrode of the electrode pad for use on a living body, wherein the gel sheet layer A of the electrode pad for use on a living body is disposed adjacent to the positive electrode, and the gel sheet layer B is disposed adjacent to the negative electrode.

(14) The electrode pad for use on a living body according to the above (12), for application of direct current.

(15) The electrotherapeutic equipment for use on a living body according to the above (13), for application of direct current.

The present specification includes the disclosure in JP patent applications No. 2016-126983 and No. 2016-193371 as a basis of the priority right of the present application.

Advantageous Effect of Invention

According to the present invention, by controlling the ratio of the amplitude S of an intermediate base to the thickness T of a gel sheet at 0.4 or less, a gel sheet having a uniform adhesive force can be obtained with a reduced variation in adhesiveness. The gel sheet is suitably used as a hydrogel sheet for attaching to the skin.

Furthermore, according to the present invention, a gel sheet capable of substantially suppressing the increase in pH and/or the decrease in conductivity can be provided even when a direct current is applied for a certain time period.

The problem to be solved, the structure and the effect other than the above will be clarified in the description of the following embodiments.

DESCRIPTION OF EMBODIMENTS

The present invention is described in detail as follows.

Figure 1:
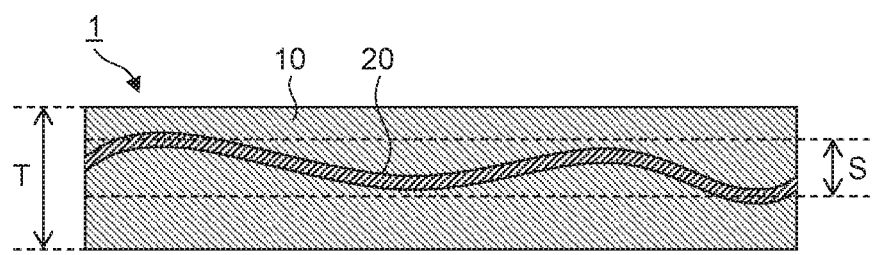
FIG. 1 is a cross-sectional view showing a gel sheet in a first embodiment of the present invention.

A cross-sectional view of a gel sheet in a first embodiment of the present invention is shown in FIG. 1. A gel sheet 1 is mainly composed of a gel material 10 and an intermediate base 20 embedded in the gel material 10. When T represents the thickness of the gel sheet 1, and S represents the amplitude of the intermediate base 20, a relation represented by the following expression (1) is satisfied:

$$S/T \leq 0.4 \tag{1}$$

Preferably, a relation represented by S/T≤0.3 is satisfied, and more preferably a relation represented by the following expression (2) is satisfied:

$$S/T \leq 0.2 \qquad (2)$$

Satisfying a relation within the range, the gel sheet 1 has very small variation in the adhesive force, so that when adhered to an adherend, easy peeling off can be prevented. Herein, the amplitude S refers to a wave height of the intermediate base 20 slightly waving in the internal part of the gel sheet 1 when observed in a cross section of the gel sheet 1, and specifically, through observation of cross sections of the parts corresponding to a width of 3 mm at three points including the center and both ends across a gel sheet having a width of 50 mm, the maximum and minimum distances from one face of the gel sheet to the intermediate base in the observation parts are measured to calculate the difference, and the average value of the obtained differences at the three points is referred to as the amplitude S. Since an intermediate base has a measurable thickness, the distance from one face of the gel sheet to the intermediate base is a measured distance from one face of the gel sheet to the center of the intermediate base in the thickness direction.

The gel material 10 is only required to have adhesiveness, and may be made from various gels without particular limitations, particularly preferably, from water-containing hydrogel. A hydrogel has excellent flexibility, water retention, etc., and can be used in various fields such as medical and pharmaceutical products, foods, civil engineering, bioengineering and sports.

As the hydrogel, various conventionally known hydrogels can be applied. For example, a hydrogel containing a polymer matrix, water and a polyhydric alcohol is preferably used.

A polymer matrix may be formed, as an example, from a copolymer of a monofunctional monomer having one ethylenically unsaturated group and a crosslinkable monomer, though not limited thereto.

As the monofunctional monomer, a water-soluble monomer such as a (meth)acrylamide monomer and a (meth)acrylate ester are preferred.

Specific examples of the (meth)acrylamide monomer include N,N-dialkyl(meth)acrylamide such as (meth)acrylamide, N,N-dimethyl(meth)acrylamide and N,N-diethyl(meth)acrylamide; N-alkyl(meth)acrylamide such as N-isopropyl(meth)acrylamide, N-methyl(meth)acrylamide, N-ethyl(meth)acrylamide, and N-propyl(meth)acrylamide; N-hydroxyalkyl(meth)acrylamide such as N-hydroxyethyl(meth)acrylamide and N-hydroxymethyl(meth)acrylamide; N-alkoxyalkyl(meth)acrylamide such as N-ethoxymethyl(meth)acrylamide, N-propoxymethyl(meth)acrylamide, N-butoxymethyl(meth)acrylamide, N-isobutoxymethyl(meth)acrylamide, N-pentoxymethyl(meth)acrylamide, N-hexyloxymethyl(meth)acrylamide, N-heptoxymethyl(meth)acrylamide, N-octoxymethyl(meth)acrylamide, N-ethoxyethyl(meth)acrylamide, N-propoxyethyl(meth)acrylamide, and N-butoxyethyl(meth)acrylamide: an amino group-containing cationic acrylamide compound such as dimethylaminopropyl(meth)acrylamide; a sulfonic acid group-containing an anionic monofunctional monomer or a salt thereof such as 4-acryloyl morpholine and tert-butylacrylamide sulfonate; and derivatives thereof. Among them, at least one selected from the group consisting of (meth)acrylamide. N,N-dimethyl(meth)acrylamide, N,N-diethyl(meth)acrylamide, N-isopropyl(meth)acrylamide, N-methyl(meth)acrylamide, N-ethyl(meth)acrylamide, N-propyl(meth)acrylamide, N-hydroxyethyl(meth)acrylamide, N-hydroxymethyl(meth)acrylamide, dimethylaminopropyl(meth)acrylamide, 4-acryloyl morpholine, tert-butylacrylamide sulfonate and salts thereof is preferably used, though not limited thereto.

Specific examples of the (meth)acrylate ester include an alkyl (meth)acrylate ester with an alkyl group having 1 to 18 carbon atoms, including an alkyl (meth)acrylate ester such as methyl (meth)acrylate, ethyl (meth)acrylate, n-propyl (meth)acrylate, isopropyl (meth)acrylate, n-butyl (meth)acrylate, isobutyl (meth)acrylate, tert-butyl (meth)acrylate, n-hexyl (meth)acrylate, n-octyl (meth)acrylate, isooctyl (meth)acrylate, 2-ethylhexyl (meth)acrylate, n-nonyl (meth)acrylate, isononyl (meth)acrylate, n-pentyl (meth)acrylae, n-decyl (meth)acrylate, isodecyl (meth)acrylate, n-lauryl (meth)acrylate, tridecyl (meth)acrylate, and n-stearyl (meth)acrylate; an alicyclic (meth)acrylate ester such as cyclohexyl (meth)acrylate, isobornyl (meth)acrylate, and 1-adamantyl (meth)acrylate; an alkoxy group-containing (meth)acrylate ester such as 2-methoxyethyl (meth)acrylate, ethoxyethoxy ethyl (meth)acrylate, and methoxypolyethylene glycol (meth)acrylate such as methoxytriethylene glycol (meth)acrylate; a hydroxyalkyl (meth)acrylate (an aryl group may be bonded to a hydroxyalkyl group through an ether bond) such as 2-hydroxyethyl (meth)acrylate, 2-hydroxypropyl (meth)acrylate, 2-hydroxy-3-phenoxypropyl (meth)acrylate, and 2-hydroxybutyl (meth)acrylate; glycerol mono(meth)acrylate; a polyalkylene glycol mono(meth)acrylate such as polyethylene glycol mono(meth)acrylate and a polyethylene glycol-polypropylene glycol copolymer; a (meth)acrylate ester having an aromatic ring such as benzyl (meth)acrylate; and a (meth)acrylate ester having a heterocyclic ring such as tetrahydrofurfuryl (meth)acrylate.

As the monofunctional monomers, (meth)acrylic acid or salts thereof, a (meth)acrylate ester, vinylpyrrolidone, vinylacetamide, a vinylamide monofunctional monomer such as vinylformamide; a nonionic monofunctional monomer such as allyl alcohol, and a styrene monomer can be used in addition to the (meth)acrylamide monomers on an as needed basis. These monofunctional monomers may be used singly or may be used in combinations of two or more. In the present specification, "(meth)acrylic" refers to acrylic or methacrylic, "(meth)acrylate" refers to acrylate or methacrylate.

The content of structural units derived from the monofunctional monomer in a hydrogel is preferably 15 parts by weight to 50 parts by weight, more preferably 15 parts by weight to 35 parts by weight, relative to 100 parts by weight of the hydrogel, though not particularly limited thereto. With an excessively small content of the structural unit derived from the monofunctional monomer relative to 100 parts by weight of the hydrogel, the hydrogel may be too soft or easily torn, having poor shape retention. With an excessively large content of the structural units derived from the monofunctional monomer relative to 100 parts by weight of hydrogel, the hydrogel may be hardened, having impaired flexibility. The content is therefore appropriately set in consideration of the balance.

As the crosslinkable monomer, it is preferable to use a monomer having two or more polymerizable double bonds in a molecule. Specific examples thereof include a polyfunctional (meth)acrylamide or (meth)acrylate such as methylenebis(meth)acrylamide, ethylenebis(meth)acrylamide. (poly)ethylene glycol di(meth)acrylate, (poly)propylene glycol di(meth)acrylate, glycerol di(meth)acrylate, and glycerol tri(meth)acrylate, tetraallyloxyethane, and diallyl ammonium chloride. These may be used singly or in combinations of two or more. Incidentally, as the cross-linkable monomer having two or more polymerizable double bonds in a molecule, a polyglycerol derivative, i.e., a polyfunctional compound having two or more (meth)acryloyl groups or vinyl groups, with a molecular weight of 400 or more, described in JP Patent No. 2803886, also may be used.

The amount of the crosslinkable monomer added is preferably in the range of 0.02 wt % to 1.5 wt %° relative to the total amount of a polymer matrix. With an excessively small amount added, the crosslinking density is low and the shape stability is poor, and in parallel, the cohesive force is reduced to lower the retention of the gel material itself, and the adhesive force is reduced in some cases. Further, when a gel sheet is peeled off, for example, a part of the gel material remains on an adherend, resulting in poor operability. With an excessively large amount of the crosslinkable monomer added, the gel may be hard and brittle with a weakened adhesive force. Herein, the polymer matrix refers to a polymerized and crosslinked matrix of the monofunctional monomer and the crosslinkable monomer.

The content of water in a hydrogel is preferably 10 to 60 parts by weight, more preferably 15 to 30 parts by weight, relative to 100 parts by weight of the hydrogel, though not particularly limited thereto. With an excessively small water content, the water content relative to the equilibrium water content of the hydrogel decreases, so that the hydrogel may change in quality (for example, swelling) over time due to enhanced hygroscopic properties. Further, with an excessively large water content, the water content relative to the equilibrium water content of the hydrogel increases, so that the hydrogel may cause contraction or changes in physical properties by drying.

The polyhydric alcohol is not particularly limited, and examples thereof include diols such as ethylene glycol, triethylene glycol, 1,6-hexanediol, 1,9-nonanediol, propylene glycol, and butanediol; trihydric or higher polyhydric alcohols such as glycerol, pentaerythritol, and sorbitol; polyhydric alcohol condensates such as polyethylene glycol, polypropylene glycol, and polyglycerol; and modified polyhydric alcohols such as polyoxyethylene glycerol.

Among the polyhydric alcohols, it is preferable to use a polyhydric alcohol in a liquid state in the operating temperature range of a hydrogel (about 20° C. for use in a room), and specifically, ethylene glycol, triethylene glycol, propylene glycol, polypropylene glycol, polyethylene glycol, polyglycerol and glycerol are preferred.

The content of the polyhydric alcohol in a hydrogel is preferably in the range of 20 to 70 parts by weight, more preferably in the range of 25 to 65 parts by weight, relative to 100 parts by weight of a hydrogel, though not particularly limited thereto. With an excessively small content of the polyhydric alcohol, the resulting hydrogel has poor moisturizing capacity and plasticity, with significant moisture evaporation, lack of stability of a hydrogel over time and lack of flexibility, so that sufficient adhesiveness cannot be achieved in some cases. With an excessively large content of the polyhydric alcohol, exceeding the amount of the polyhydric alcohol that the polymer matrix can hold, the polyhydric alcohol bleeds out from the surface of the hydrogel to cause fluctuation in physical properties, so that sufficient adhesiveness may not be achieved in some cases. The content is therefore appropriately set in consideration of the balance.

Also, the gel material 10 may contain an electrolyte to impart conductivity to a gel material on an as needed basis.

In the case of imparting conductivity to a gel material, the content of the electrolyte in the gel material is preferably 0.05 to 10 parts by weight, more preferably 0.1 to 6 parts by weight, relative to 100 parts by weight of the gel material. With an excessively small content of the electrolyte, the impedance increases, so that conductivity cannot be good. The impedance decreases as the content of the electrolyte increases. With an excessively large content of the electrolyte, however, the impedance no longer decreases, resulting in wasteful costs.

The electrolyte is not particularly limited, and examples thereof include an alkali metal halide such as sodium halide (e.g. sodium chloride), a lithium halide, and a potassium halide; an alkaline earth metal halide such as magnesium halide and calcium halide; and other metal halides. A hypochlorite, a chlorite, a chlorate, a perchlorate, a sulfate, a carbonate, a nitrate, or a phosphate of various metals also is suitably used as the electrolyte. Further, inorganic salts such as ammonium salts and various complex salts; salts of monovalent organic carboxylic acids such as acetic acid, benzoic acid, and lactic acid; salts of polyvalent organic carboxylic acids such as tartaric; mono-, di- or more-valent salts of polyvalent carboxylic acids such as phthalic acid, succinic acid, adipic acid and citric acid; metal salts of organic acids such as sulfonic acids and amino acids; and organic ammonium salts are also suitable as the electrolyte.

Further, to the gel material 10, a base such as sodium hydroxide may be appropriately added for the purpose of adjusting the pH.

Further, the gel material 10 may contain other additives on an as needed basis. Examples of the other additives include a rust inhibitor, an antifungal, an antioxidant, an antifoaming agent, a stabilizer, a surfactant, and a coloring agent.

The gel material 10 can be obtained by dissolving or uniformly dispersing the materials described above, a polymerization initiator, and a solvent, etc. and applying heat, UV radiation, or the like to the mixture to be polymerized and crosslinked. The polymerization initiator may be a thermal polymerization initiator or a photo polymerization initiator. The content of the polymerization initiator is preferably 0.01 parts by weight or more and preferably 1 part by weight or less, relative to 100 parts by weight excluding the polymerization initiator from the composition (liquid monomer mixture) before polymerization, though not particularly limited thereto. Furthermore, in the case of polymerization by UV irradiation, the integrated dose of UV radiation is, for example, preferably in the range of 1000 mJ/cm$^2$ to 10000 mJ/cm$^2$, more preferably in the range of 2000 mJ/cm$^2$ to 10000 mJ/cm$^2$, though it varies depending on the content of the polymerization initiator and the like.

The intermediate base 20 to be embedded in the gel material 10 is used to reinforce the gel sheet and improve the shape retention in cutting and the like, and may be composed of a nonwoven fabric or a woven fabric in a specific aspect. The material for use as the nonwoven fabric or the woven fabric may be made of a natural fiber such as cellulose, silk, and hemp, synthetic fiber such as polyester, nylon, rayon, polyethylene, polypropylene and polyurethane, or a mixed yarn thereof. On an as needed basis, a binder may be used in the material, and further, on an as needed basis, the material may be colored. Alternatively, as the intermediate base 20, a membrane selected from the group consisting of a semipermeable membrane, an ion exchange membrane, a microfiltration membrane, an ultrafiltration membrane and a nanofiltration membrane, and the like may be used.

Examples of the method for producing the non-woven fabric include a dry method, a wet method, a spun bond method, a melt-blown method, an air-laid method, a chemical bonding method, a thermal bonding method, a needle-punching method, and a hydroentangling method, though not particularly limited thereto. To employ a process corresponding to the basis weight and the material, with the fabric having no variation in the basis weight, is more preferable for the position control of the intermediate base. In the case of woven fabric, plain weave, tricot, raschel, etc., can be appropriately selected without particular limitations.

Also, the basis weight of the woven or nonwoven fabric is not particularly limited as long as predetermined physical properties of an intermediate base can be obtained, being, for example, preferably 10 to 40 $g/m^2$, more preferably 10 to 28 $g/m^2$. With an excessively small basis weight of the woven or nonwoven fabric, the reinforcement of a gel sheet, and the like may not be achieved, or due to the increased variation in the basis weight, liquid permeability during producing the gel sheet varies depending on the location, so that the position of the intermediate base may vary. With an excessively large basis weight, the intermediate base 20 is hardened, so that followability of the gel sheet 1 to the skin may be impaired or the conductivity may suffer negative effects. The basis weight is therefore appropriately set in consideration of the balance.

With an excessively large thickness of the intermediate base 20, the liquid permeability is degraded, so that the conductivity may suffer negative effects. On the contrary, whereas with an excessively small thickness, the reinforcement of a gel sheet, and the like may not be achieved, or the position of the intermediate base may vary, as in the case of an excessively small basis weight. The thickness is therefore appropriately set in consideration of the circumstances. The thickness is preferably in the range of 0.05 mm to 2.0 mm, more preferably 0.05 mm to 0.5 mm, and particularly preferably 0.08 mm to 0.3 mm.

With an excessively large thickness of the gel sheet 1, shear stress decreases to an inadequate level. With an excessively small thickness, the cohesive force decreases and the gel surface may be destroyed. A suitable thickness is selected in consideration of the circumstances. The thickness is preferably in the range of 0.2 mm to 2.0 mm, particularly preferably 0.3 mm to 1.2 mm, more preferably 0.3 mm to 1.0 mm.

The method for producing a gel sheet 1 is not particularly limited, as the detailed conditions vary depending on the composition of the gel material, the material and thickness of the intermediate base, etc. For example, the following methods may be appropriately employed: a method including holding an intermediate base with a tension higher than a certain level applied in the air such that the amplitude of the intermediate base is minimized, casting a liquid monomer mixture above and below the intermediate base, and forming a sheet by polymerization with light irradiation or the like; a method including preparing two sheets of sheet-like gel material having a smooth surface, and then holding an intermediate base held with a tension higher than a certain level applied between the two sheets of gel material to make a composite; a method including preparing a sheet-like gel material having a smooth surface, placing an intermediate base with a tension higher than a certain level applied on the sheet of gel material, casting a liquid monomer mixture on the intermediate base, and further polymerizing the monomers by light irradiation or the like, and the like. In the case where the polymerization is performed in a continuous production process, a sheet may be taken out after making a roll.

On an as needed basis, one face of the gel sheet 1 may be provided with a base film, and the rear face to the opposite side of the base film may be provided with a top film.

Examples of the base film for use include a resin film made of polyester, polyolefin, polystyrene, or polyurethane, paper, and paper laminated with the resin film.

Preferably, the surface of the base film in contact with the gel sheet 1 is subjected to release treatment. Examples of the release treatment method include silicone coating, and, in particular, baked silicone coating crosslinked and cured by heat or UV radiation is preferred. As the film to be subjected to release treatment, a biaxially stretched PET (polyethylene terephthalate) film, and an OPP (oriented polypropylene) film are particularly preferred.

As the top film, the same material as the base film may be basically used. In the case where the polymerization is performed by UV irradiation and the like with a top film provided, however, it is preferable to select a film material that does not block light, such that photopolymerization is not inhibited.

The gel sheet as described above has no variation in adhesive force due to inclusion of the intermediate base with the amplitude controlled, so that is suitably used for applications requiring uniform adhesiveness. For example, the gel sheet can be used as a hydrogel sheet to be attached to the skin, such as a wound dressing, an adhesive for use on a living body, or a bioelectrode. Examples of other suitable uses include a substrate of percutaneous absorbent impregnated with a chemical, industrial applications such as an electrode material in industrial instruments and industrial adhesive, applications in construction such as nonpolar electrode placed on the surface of the ground or bedrock for electric geological survey, a conductive material for detecting breakage of a water shield sheet and the like used in waste treatment plants, and a conductive adhesive material installed between a concrete structure and a metal as positive electrode in a method for electrolytic protection of a concrete structure.

The second and third embodiments of the gel sheet of the present invention are described in detail as follows.

A second embodiment and a third embodiment of the present invention relate to a gel sheet having at least two gel sheet layers. The gel sheets in the second and third embodiments of the present invention are shown in FIG. 2 and FIG. 3, respectively.

Figure 2:
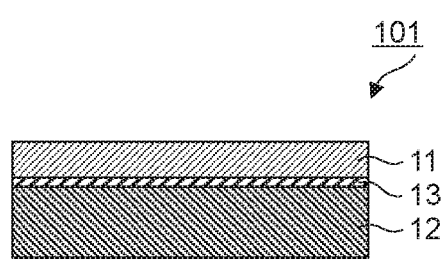
FIG. 2 is a cross-sectional view showing a gel sheet in a second embodiment of the present invention.
Figure 3:
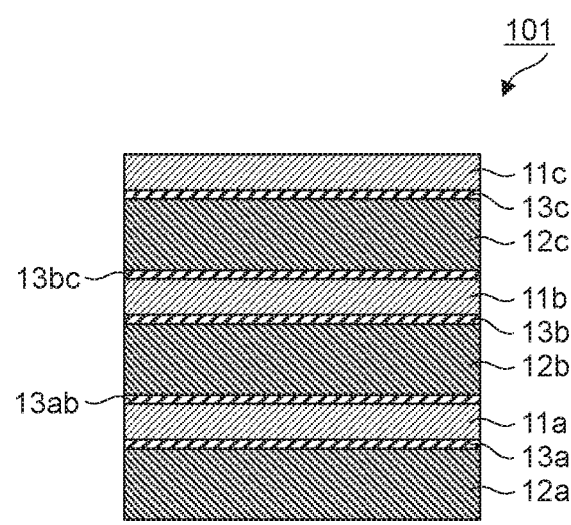
FIG. 3 is a cross-sectional view showing a gel sheet in a third embodiment of the present invention.

As shown in FIG. 2, a gel sheet 101 of the present aspect comprises at least two gel sheet layers including a gel sheet layer A 11 and a gel sheet layer B 12 made of, for example, hydrogel, respectively. In the gel sheet 101 of the present aspect, on the top face of the gel sheet layer B 12, the gel sheet layer A 11 is disposed, so that the gel sheet layer A 11 and the gel sheet layer B 12 are disposed so that they are alternately stacked.

In the case where two or more gel sheet layers A and two or more gel sheet layers B are present, respectively, in the gel sheet of the present aspect, the two or more gel sheet layers A may have the same dimensions and/or composition, respectively, or may have dimensions and/or composition different from each other, within the range of features disclosed in the present specification. Also, the two or more gel sheet layers B may have the same dimensions and/or composition, respectively, or may have dimensions and/or composition different from each other, within the range of features disclosed in the present specification.

In the gel sheet of the present aspect, the gel sheet layer A contains at least one inorganic salt with a predetermined content. Also, the gel sheet layer B contains at least one inorganic salt with a predetermined content or contains no inorganic salt. Since the gel sheet layer A contains at least one inorganic salt with a predetermined content, the gel sheet of the present aspect can have conductivity as a whole.

When the total content of the at least one inorganic salt contained in the gel sheet layer A relative to the total weight of the gel sheet layer A is represented by X wt %, and the total content of the at least one inorganic salt contained in the gel sheet layer B relative to the total weight of the gel sheet layer B is represented by Y wt %, Y is less than X. In other words, the total content Y of the at least one inorganic salt contained in the gel sheet layer B is less than the total content X of the at least one inorganic salt contained in the gel sheet layer A. The present inventors found that in the gel sheet of the present aspect of having Y of less than X, with the gel sheet layer A disposed adjacent to the positive electrode, and the gel sheet layer B containing at least one acid to be described below disposed adjacent to the negative electrode, the increase in pH and the decrease in conductivity were substantially suppressed when a direct current was applied for a certain time period. It is conceivable that the effect in the gel sheet of the present aspect was achieved by the following. In the gel sheet layer B containing a small amount of inorganic salt or not containing inorganic salt, the progress of electrolysis is substantially suppressed, so that the increase in pH and the generation of bubbles are substantially suppressed. On the other hand, the gel sheet layer A contains a large amount of inorganic salt, so that the conductivity can be substantially maintained. In the case where the gel sheet of the present aspect is applied, for example, to an electrode pad or in various equipment with use of the electrode pad, therefore, the increase in pH and the decrease in conductivity can be substantially avoided to achieve stable use of the electrode pad and the equipment, even when a direct current is applied for a certain time period.

In the gel sheet of the present aspect, preferably X and Y satisfy the following expression (3):

$$0 \leq Y < X \leq 15 \quad (3)$$

The total content of the at least one inorganic salt contained in the gel sheet layer B may be 0 or more. In other words, the gel sheet layer B may not contain inorganic salt. On the other hand, the total content of the at least one inorganic salt contained in the gel sheet layer A is in a range exceeding 0, so that the gel sheet of the present aspect can have conductivity as a whole. In the case where Y is in a range exceeding X, when a direct current is applied to the gel sheet of the present aspect with the gel sheet layer A disposed adjacent to the positive electrode for a certain time period, electrolysis proceeds in the gel sheet layer B, so that increase in pH and/or the generation of bubbles may occur. X is preferably in the range of 2 to 15 wt %, more preferably in the range of 2 to 8 wt %. Y is less than X, and further, preferably in the range of 0 or more and less than 15 wt %, more preferably in the range of 0 or more and less than 8 wt %. In the case of X of less than 2 wt %, sufficient conductivity may not be exhibited. In the case of X of more than 15 wt %, sufficient increase in the effect may not be achieved even when the content of inorganic salt increases. In the case where X and Y satisfy the expression (3), therefore, the gel sheet of the present aspect can substantially suppress the increase in pH and the decrease in conductivity even when a direct current is applied for a certain time period.

The at least one inorganic salt contained in the gel sheet layer A and the gel sheet layer B is not limited, and examples thereof include an alkali metal halide such as sodium halide (e.g. sodium chloride), a lithium halide, and a potassium halide; an alkaline earth metal halide such as magnesium halide and calcium halide; and other metal halides. A hypochlorite, a chlorite, a chlorate, a perchlorate, a sulfate, a carbonate, a nitrate, or a phosphate of various metals also is suitably used as the inorganic salt. Alternatively, inorganic salts such as ammonium salts and various complex salts are also suitably used. As the at least one inorganic salt contained in the gel sheet layer A and the gel sheet layer B, these inorganic salts may be used singly, or in combinations of two or more.

In the gel sheet of the present aspect, the type and the total content of the at least one inorganic salt contained in the gel sheet layer A, and the type and the total content of the at least one inorganic salt contained in the gel sheet layer B, is not limited, and can be determined, for example, through quantitative analysis of the at least one inorganic salt contained in a predetermined weight of sample taken out from the gel sheet layer A or the gel sheet layer B by analytical means such as ICP emission spectral analysis, atomic absorption spectrometry or ion chromatography method.

In the gel sheet of the present aspect, the gel sheet layer B contains at least one acid. Examples of the at least one acid include an organic acid, an inorganic acid, and a mixture thereof. Preferably the at least one acid comprises an organic acid, and more preferably the at least one acid is an organic acid. Examples of the organic acid include formic acid, acetic acid, propionic acid, butyric acid, valeric acid, caproic acid, caprylic acid, capric acid, phthalic acid, oxalic acid, lactic acid, tartaric acid, fumaric acid, maleic acid, succinic acid, citric acid, malic acid, glutaric acid, adipic acid, amino acid, ascorbic acid, benzoic acid, salicylic acid and polyacrylic acid. The content of the at least one acid in the gel sheet layer B relative to the total weight of the gel sheet layer B is, preferably 10 wt % or less, more preferably in the range of 0.01 to 10 wt %, still more preferably in the range of 0.1 to 2 wt %. Since the gel sheet layer B contains the at least one acid, the pH of the gel sheet layer B can be controlled in the preferred range. Thereby, the gel sheet of the present aspect can substantially suppress the increase in pH even when a direct current is applied for a certain time period.

The gel sheet layer A may contain a weakly basic substance such as chitosan, weakly basic amino acid or cationic polymer for the purpose of suppressing the fluctuation of pH.

In the gel sheet of the present aspect, the type and the content of the at least one acid contained in the gel sheet layer A, and the type and the content of the at least one acid contained in the gel sheet layer B, can be determined through quantitative analysis of the at least one acid contained in a predetermined weight of sample taken out from the gel sheet layer A or the gel sheet layer B by analytical means. Although the analytical means is not limited, for example, in the case of an organic acid, analytical means such as high performance liquid chromatography (HPLC), gas chromatography (GC), liquid chromatography/mass spectrometry (LC/MS), ion chromatography/mass spectrometry (IC/MS) or gas chromatography/mass spectrometry (GC/MS) can be used and in the case of an inorganic acid, analytical means such as ICP emission spectral analysis, atomic absorption spectrometry or ion chromatography method can be used.

In the gel sheet of the present aspect, a hydrogel can be used as the gel material to constitute the gel sheet layer A and the gel sheet layer B. Various hydrogels known in the art can be applied as the hydrogels. In the present specification, "hydrogel" refers to a swelling material in a gel form comprising a polymer matrix having a three-dimensional network structure and water molecules present in the network structure. The hydrogel typically comprises a polymer matrix, water and a polyhydric alcohol.

The polymer matrix to constitute the hydrogel is not limited, and may be formed from, for example, a copolymer of a monofunctional monomer having one ethylenic unsaturated group and a crosslinkable monomer.

The monofunctional monomer is preferably a water-soluble monomer such as a (meth)acrylamide monomer or a (meth)acrylate ester. In the present specification, "(meth) acrylic" refers to acrylic or methacrylic, "(meth)acrylate" refers to acrylate or methacrylate.

Specific examples of the (meth)acrylamide monomer include N,N-dialkyl(meth)acrylamide such as (meth)acrylamide, N,N-dimethyl(meth)acrylamide and N,N-diethyl (meth)acrylamide; N-alkyl(meth)acrylamide such as N-isopropyl(meth)acrylamide, N-methyl(meth)acrylamide, N-ethyl(meth)acrylamide and N-propyl(meth)acrylamide; N-hydroxyalkyl(meth)acrylamide such as N-hydroxyethyl (meth)acrylamide and N-hydroxymethyl(meth)acrylamide; N-alkoxyalkyl(meth)acrylamide such as N-ethoxymethyl (meth)acrylamide, N-propoxymethyl(meth)acrylamide, N-butoxymethyl(meth)acrylamide, N-isobutoxymethyl (meth)acrylamide, N-pentoxymethyl(meth)acrylamide, N-hexyloxymethyl(meth)acrylamide, N-heptoxymethyl (meth)acrylamide, N-octoxymethyl(meth)acrylamide, N-ethoxyethyl(meth)acrylamide, N-propoxyethyl(meth) acrylamide and N-butoxyethyl(meth)acrylamide: an amino group-containing cationic acrylamide compound such as dimethylaminopropyl(meth)acrylamide; a sulfonic acid group-containing anionic monofunctional monomer or a salt thereof such as 4-acryloyl morpholine and tert-butyl acrylamide sulfonate; and derivatives thereof. The (meth)acrylamide monomer is, though not limited, preferably at least one compound selected from the group consisting of (meth) acrylamide, N,N-dimethyl(meth)acrylamide, N,N-diethyl (meth)acrylamide, N-isopropyl(meth)acrylamide. N-methyl (meth)acrylamide, N-ethyl(meth)acrylamide, N-propyl (meth)acrylamide, N-hydroxyethyl(meth)acrylamide, N-hydroxymethyl(meth)acrylamide, dimethylaminopropyl (meth)acrylamide, 4-acryloyl morpholine and tert-butylacrylamide sulfonate, and salts thereof.

Specific examples of the (meth)acrylate ester include an alkyl (meth)acrylate ester with an alkyl group having 1 to 18 carbon atoms, including an alkyl (meth)acrylate ester such as methyl (meth)acrylate, ethyl (meth)acrylate, n-propyl (meth)acrylate, isopropyl (meth)acrylate, n-butyl (meth) acrylate, isobutyl (meth)acrylate, tert-butyl (meth)acrylate, n-hexyl (meth)acrylate, n-octyl (meth)acrylate, isooctyl (meth)acrylate, 2-ethylhexyl (meth)acrylate, n-nonyl (meth) acrylate, isononyl (meth)acrylate, n-pentyl (meth)acrylae, n-decyl (meth)acrylate, isodecyl (meth)acrylate, n-lauryl (meth)acrylate, tridecyl (meth)acrylate, and n-stearyl (meth) acrylate; an alicyclic (meth)acrylate ester such as cyclohexyl (meth)acrylate, isobornyl (meth)acrylate, and 1-adamantyl (meth)acrylate; an alkoxy group-containing (meth)acrylate ester such as 2-methoxyethyl (meth)acrylate, ethoxyethoxyethyl (meth)acrylate, and methoxypolyethylene glycol (meth)acrylate such as methoxytriethylene glycol (meth) acrylate; a hydroxyalkyl (meth)acrylate (an aryl group may be bonded to a hydroxyalkyl group through an ether bond) such as 2-hydroxyethyl (meth)acrylate, 2-hydroxypropyl (meth)acrylate, 2-hydroxy-3-phenoxypropyl (meth)acrylate, and 2-hydroxybutyl (meth)acrylate; glycerol mono(meth) acrylate; a polyalkylene glycol mono(meth)acrylate such as polyethylene glycol mono(meth)acrylate and a polyethylene glycol-polypropylene glycol copolymer; a (meth)acrylate ester having an aromatic ring such as benzyl (meth)acrylate; and a (meth)acrylate ester having a heterocyclic ring such as tetrahydrofurfuryl (meth)acrylate.

As the monofunctional monomers. (meth)acrylic acid or salts thereof, a (meth)acrylate ester, vinylpyrrolidone, vinylacetamide, a vinylamide monofunctional monomer such as vinylformamide; a nonionic monofunctional monomer such as allyl alcohol, and a styrene monomer can be used in addition to the (meth)acrylamide monomers exemplified above on an as needed basis. These monofunctional monomers may be used singly or may be used in combinations of two or more.

The content of structural units derived from the monofunctional monomer in a hydrogel to constitute the gel sheet layer A and the gel sheet layer B is preferably in the range of 10 parts by weight to 50 parts by weight, more preferably 10 parts by weight to 35 parts by weight, relative to 100 parts by weight of the hydrogel, though not limited thereto. With a content of the structural unit derived from the monofunctional monomer of less than the lower limit, the hydrogel may be too soft or easily torn, having poor shape retention. With a content of the structural units derived from the monofunctional monomer of more than the upper limit, the hydrogel may be hardened, having impaired flexibility. With a content of the structural units derived from the monofunctional monomer in the range, therefore, a predetermined shape can be maintained and a predetermined flexibility can be achieved.

As the crosslinkable monomer, a monomer having two or more polymerizable double bonds in a molecule is preferable. Specific examples of the crosslinkable monomer include a polyfunctional (meth)acrylamide or (meth)acrylate such as methylenebis(meth)acrylamide, ethylenebis(meth) acrylamide, (poly)ethylene glycol di(meth)acrylate, (poly) propylene glycol di(meth)acrylate, glycerol di(meth)acrylate, or glycerol tri(meth)acrylate, tetraallyloxyethane, and diallyl ammonium chloride. These crosslinkable monomers may be used singly or in combinations of two or more. Alternatively, as the crosslinkable monomer having two or more polymerizable double bonds in a molecule, a polyglycerol derivative. i.e., a polyfunctional compound having two or more (meth)acryloyl groups or vinyl groups, with a molecular weight of 400 or more, described in JP Patent No. 2803886, also may be used.

The content of the crosslinkable monomer in the hydrogel to constitute the gel sheet layer A and the gel sheet layer B is preferably in the range of 0.0005 to 0.5 parts by weight, more preferably in the range of 0.001 to 0.2 parts by weight, still more preferably in the range of 0.001 to 0.1 parts by weight relative to 100 parts by weight of the hydrogel. With an amount of the crosslinkable monomer added of less than the lower limit, the crosslinking density is low and the shape stability is poor, and in parallel, the cohesive force is reduced to lower the retention of the hydrogel itself, and the adhesive force may be reduced in some cases. Further, when the gel sheet is brought into contact with an adherend of living body (e.g., skin) and subsequently peeled off from the adherend, a part of the hydrogel may remain on the adherend. In this case, the operability of the gel sheet of the present aspect may be poor in some cases. With an amount of the crosslinkable monomer added of more than the upper limit, the gel may be hard and brittle with a weakened adhesive force. Herein, the polymer matrix defined above refers to a matrix formed by polymerization and crosslinking of the monofunctional monomer and the crosslinkable monomer.

The content of water in the hydrogel to constitute the gel sheet layer A and the gel sheet layer B is preferably in the range of 10 to 60 parts by weight, more preferably in the range of 15 to 50 parts by weight, particularly preferably in the range of 15 to 40 parts by weight, relative to 100 parts by weight of the hydrogel, though not particularly limited thereto. With a water content of less than the lower limit, the water content relative to the equilibrium water content of the hydrogel decreases, so that the hydrogel may change in quality (for example, swelling) over time due to enhanced hygroscopic properties. Further, with a water content of more than the upper limit, the water content relative to the equilibrium water content of the hydrogel increases, so that the hydrogel may cause contraction or changes in physical properties by drying. With a water content in the range, therefore, the change in physical properties such as moisture absorption or contradiction of the hydrogel can be substantially suppressed.

In the gel sheet of the present aspect, when the gel sheet layer B has a water content of α wt % relative to the total weight of the gel sheet layer B, Y and a preferably satisfy the following expression (4):

$$0 \leq Y/\alpha \leq 0.03 \quad (4)$$

Y/α is preferably 0.02 or less, more preferably 0.01 or less. In the case of Y/α exceeding 0.03, when a direct current is applied to the gel sheet of the present aspect, with the gel sheet layer A disposed adjacent to the positive electrode for a certain time period, electrolysis proceeds in the gel sheet layer B, so that the increase in pH and/or the generation of bubbles may occur. In the case where Y and a satisfy the expression (4), therefore, the gel sheet of the present aspect can substantially suppress the increase in pH and the decrease in conductivity even when a direct current is applied for a certain time period.

In the gel sheet of the present aspect, the water content in the gel sheet layer A and the water content in the gel sheet layer B are note limited, and can be determined, for example, by drying a predetermined weight of sample taken out from the gel sheet layer A or the gel sheet layer B so as to measure the dry weight and calculate the difference between the initial weight and the dry weight, or to measure by a volumetric titration method or a coulometric titration method using a Karl Fischer moisture measurement apparatus.

Examples of the polyhydric alcohol include diols such as ethylene glycol, triethylene glycol, 1,6-hexanediol, 1,9-nonanediol, propylene glycol, and butanediol; trihydric or higher polyhydric alcohols such as glycerol, pentaerythritol, and sorbitol; polyhydric alcohol condensates such as polyethylene glycol, polypropylene glycol, and polyglycerol; and modified polyhydric alcohols such as polyoxyethylene glycerol, though not particularly limited thereto. Among the polyhydric alcohols, it is preferable to use a polyhydric alcohol in a liquid state in the operating temperature range of a hydrogel (about 20° C. for use in a room). As the polyhydric alcohol, for example, ethylene glycol, triethylene glycol, propylene glycol, polypropylene glycol, polyethylene glycol, polyglycerol or glycerol is preferred.

The content of the polyhydric alcohol in the hydrogel to constitute the gel sheet layer A and the gel sheet layer B is preferably in the range of 20 to 70 parts by weight, more preferably in the range of 20 to 65 parts by weight, relative to 100 parts by weight of a hydrogel, though not limited thereto. With a content of the polyhydric alcohol of less than the lower limit, the resulting hydrogel has poor moisturizing capacity and plasticity, with significant moisture evaporation, lack of stability of the hydrogel over time and lack of flexibility, so that sufficient adhesiveness cannot be achieved in some cases. With a content of the polyhydric alcohol of more than the upper limit, exceeding the amount of the polyhydric alcohol that the polymer matrix can hold, the polyhydric alcohol bleeds out from the surface of the hydrogel to cause fluctuation in physical properties, so that sufficient adhesiveness may not be achieved in some cases. With a content of the polyhydric alcohol in the range, the change in physical properties such as reduction in adhesiveness of the hydrogel and the fluctuation in physical properties such as bleeding out of the polyhydric alcohol can be substantially suppressed.

In the gel sheet of the present aspect, the pH of the gel sheet layer A and the gel sheet layer B is usually in the range of weak acidity to neutrality, for example, in the range of 3 to 8. The pH of the gel sheet layer A is preferably in the range of 3 to 8, and more preferably in the range of 4 to 7. The pH of the gel sheet layer B is preferably in the range of 3 to 8, and more preferably in the range of 4 to 7. With a pH of the gel sheet layer A and the gel sheet layer B in the range, in particular, with a pH of the gel sheet layer B in the range, the gel sheet of the present aspect can substantially suppress the increase in pH even when a direct current is applied for a certain time period.

In the gel sheet of the present aspect, the gel sheet layer A and the gel sheet layer B may contain other additives if desired. Examples of the other additives include a buffer, a rust inhibitor, an antifungal, an antioxidant, an antifoaming agent, a stabilizer, a surfactant, and a coloring agent. A buffer such as an organic salt electrolyte is preferred as the other additive. In the case where a gel sheet layer A and/or a gel sheet layer B contain a buffer, buffer capacity can be imparted to the gel sheet layer A and/or the gel sheet layer B. Containing other additives, the gel sheet layer A and the gel sheet layer B can impart the gel sheet of the present aspect with various characteristics.

In the gel sheet of the present aspect, when the gel sheet layer A has a thickness of a (mm), and the hydrogel sheet layer B has a thickness of b (mm), it is preferable that a and b satisfy the following expressions (5) and (6):

$$b/a \geq 1 \quad (5)$$

$$0.6 \leq a+b \leq 3.0 \quad (6)$$

In the gel sheet of the present aspect, in the case of b/a of less than 1 or in the case of a+b of less than 0.6, with the gel sheet layer A disposed adjacent to the positive electrode, when a direct current is applied for a certain time period, electrolysis proceeds in the gel sheet layer B, so that the increase in pH and/or the generation of bubbles may occur. In the case of a+b exceeding 3.0, a significant effect corresponding to the thickness may not be achieved. Further, when the gel sheet of the present aspect is applied to an electrode pad, workability may be reduced. With a and b satisfying the expressions (5) and (6), therefore, the gel sheet of the present aspect can substantially suppress the increase in pH and the decrease in conductivity even when a direct current is applied for a certain time period. Incidentally, the thickness of the gel sheet layer A and the gel sheet layer B may be determined by measurement using, for example, a micrometer, though not limited thereto. In the case where a top film and/or a base film to be described below are disposed on the outer surfaces of the gel sheet layer A and the gel sheet layer B, the top film and/or the base film may be removed for the measurement to measure the thicknesses of the gel sheet layer A and the gel sheet layer B by the means described above.

In the gel sheet of the present aspect, the numbers of the gel sheet layer A and the gel sheet layer B may be one or more, respectively, and the upper limit is not particularly limited. The numbers of the gel sheet layer A and the gel sheet layer B are, for example, in the range of 1 to 3, respectively. For example, as shown in the third embodiment in FIG. 3, a gel sheet 101 can have six gel sheet layers in total including three gel sheet layers A 11a, 11b and 11c and three gel sheet layers B 12a, 12b and 12c. In the present embodiment, on the top face of the gel sheet layer B 12a, the gel sheet layer A 11a is disposed; on the top face of the gel sheet layer A 11a, the gel sheet layer B 12b is disposed; on the top face of the of the gel sheet layer B 12b, the gel sheet layer A 11b is disposed; on the top face of the of the gel sheet layer A 11b, the gel sheet layer B 12c is disposed; and on the top face of the of the gel sheet layer B 12c, the gel sheet layer A 11c is disposed; so that the gel sheet layers A 11a. 11b and 11c and gel sheet layers B 12a, 12b and 12c can be disposed so as to be alternately stacked.

In the gel sheet of the present aspect, an intermediate base is embedded between the gel sheet layer A and the gel sheet layer B. When T represents the thickness of the gel sheet, and S represents the amplitude of the intermediate base, a relation represented by the following expression (1) is satisfied as described in the first embodiment:

$$S/F \leq 0.4 \qquad (1)$$

Specifically, as shown in FIG. 2, in a gel sheet 101 of the present aspect, a membrane 13 as intermediate base is further disposed between a gel sheet layer A 11 and a gel sheet layer B 12. In the case where the gel sheet of the present aspect comprises two or more gel sheet layers A and two or more gel sheet layers B, it is preferable that the membranes be disposed between the gel sheet layers A and the gel sheet layers B, respectively. For example, as shown in FIG. 3, the gel sheet 101 of the present aspect comprises six gel sheet layers in total including three gel sheet layers A 11a, 11b, 11c and three gel sheet layers B 12a, 12b and 12c, and membranes 13a, 13b, 13c, 13ab and 13bc can be further disposed between the respective gel sheet layers A 11a, 11b, 11c and three gel sheet layers B 12a, 12b and 12c. In the case of the present embodiment, the gel sheet layer A 11a is disposed on the top face of the gel sheet layer B 12a, the gel sheet layer B 12b is disposed on the top face of the gel sheet layer A 11a, the gel sheet layer A 11b is disposed on the top face of the gel sheet layer B 12b, the gel sheet layer B 12c is disposed on the top face of the gel sheet layer A 11b, and the gel sheet layer A 11c is disposed on the top face of the gel sheet layer B 12c, so that the gel sheet layers A 11a, 11b and 11c and the gel sheet layers B 12a, 12b and 12c are alternately stacked. Further, the membrane 13a can be disposed between the gel sheet layer A 11a and the gel sheet layer B 12a, the membrane 13b can be disposed between the gel sheet layer A 11b and the gel sheet layer B 12b, the membrane 13c can be disposed between the gel sheet layer A 11c and the gel sheet layer B 12c, the membrane 13ab can be disposed between the gel sheet layer A 11a and the gel sheet layer B 12b, and the membrane 13bc can be disposed between the gel sheet layer A 11b and the gel sheet layer B 12c.

The membrane is typically selected from the group consisting of a semipermeable membrane, an ion exchange membrane, a microfiltration membrane, an ultrafiltration membrane and a nanofiltration membrane. A membrane selected from the group consisting of, for example, a semipermeable membrane such as cellophane and cellulose acetate, and an ion exchange membrane such as a cation exchange membrane and an anion exchange membrane is preferred though not limited thereto; a membrane of cellophane or an anion exchange membrane is more preferred; and a membrane of cellophane is still more preferred. In the present embodiment, material transfer between the gel sheet layer A and the gel sheet layer B is substantially suppressed by the membrane. The gel sheet of the present embodiment, therefore, enables the effect to suppress the increase in pH and the decrease in conductivity to be exhibited for a longer period.

The surface area of a membrane is preferably 80% or more of the surface area of the gel sheet layer A at the laminated face of the gel sheet layer A and the gel sheet layer B where the membrane is disposed, more preferably 90% or more, still more preferably approximately 100%. With a surface area of the membrane in the range, material transfer between the gel sheet layer A and the gel sheet layer B is substantially suppressed. The gel sheet of the present embodiment, therefore, enables the effect to suppress the increase in pH and the decrease in conductivity to be exhibited for a longer period.

In a gel sheet of the present aspect, in order to reinforce the gel sheet and/or improve the shape retention in cutting, an intermediate base made from material for use in the art may be employed instead of the membrane described above. For example, the intermediate base may be composed of a nonwoven fabric or woven fabric described in the first embodiment. The material of the intermediate base may be appropriately selected from ones for use as conventional intermediate base of a hydrogel in the art. Examples of the material of the nonwoven fabric or woven fabric for use as an intermediate base include a natural fiber such as cellulose, silk, and hemp, synthetic fiber such as polyester, nylon, rayon, polyethylene, polypropylene and polyurethane, or a mixed yarn thereof. On an as needed basis, an intermediate base may comprise a binder. Also, on an as needed basis, an intermediate base may be colored. Since the gel sheet layer A and/or the gel sheet layer B comprise an intermediate base, the strength and/or the shape retention in cutting of the gel sheet of the present aspect can be improved.

In the gel sheet of the present aspect, a top film may be disposed on the outer surface of the gel sheet layer A, if desired. Also, a base film may be disposed on the outer surface of the gel sheet layer B, if desired. Preferably the top film and the base film are disposed to cover approximately the whole outer surface of the gel sheet layer A or the gel sheet layer B. Since in the gel sheet of the present aspect, the top film and the bottom film is disposed, the outer surfaces of the gel sheet layer A and the gel sheet layer B can be protected from contamination and/or drying or the like until use.

Examples of the base film for use include a resin film made of polyester, polyolefin, polystyrene, or polyurethane, paper, or paper laminated with the resin film. Preferably, the surface of the base film in contact with outer surface of the gel sheet layer B is subjected to release treatment. Examples of the release treatment method include silicone coating, and, in particular, baked silicone coating through crosslinking and curing reaction by heat or UV radiation is preferred. As the film to be subjected to release treatment, a biaxially stretched polyethylene terephthalate (PET) film, or an oriented polypropylene (OPP) film, or the like are particularly preferred.

As the top film, the same material exemplified as the base film may be applied. In the case where the monomers to constitute the gel sheet are polymerized by UV irradiation and the like through a top film disposed on the outer surface of the gel sheet layer A, it is preferable to select a film material that does not block light. Using a top film made of such a material, polymerization of the monomers can be accomplished without interruption to the photopolymerization.

The method for polymerizing monomers in the gel sheet of the present aspect includes a redox polymerization, a radical polymerization, and a radiation polymerization, though not particularly limited thereto. In a radical polymerization, the gel sheet layer A and the gel sheet layer B can be obtained by dissolving or dispersing each of the materials including monomers and a polymerization initiator in a solvent or the like, and applying heat or UV irradiation to the resulting liquid monomer mixture to cause polymerization and crosslinking of the material comprising monomers. Although the polymerization initiator may be any one of a photopolymerization initiator and a thermal polymerization initiator, in the case of a sheet having a thickness of, for example, a few micrometers to a few millimeters, a radical polymerization by ultraviolet light with use of a photopolymerization initiator is preferred. Examples of the photopolymerization initiator include 2-hydroxy-2-methyl-1-phenyl-propan-1-one, 1-[4-(2-hydroxyethoxy)-phenyl]-2-hydroxy-2-methyl-1-propan-1-one, 22-hydroxy-{-(4-[4-(2-hydroxy-2-methyl-propionyl)-benzyl]phenyl}-2-methyl-propan-1-one, 1-hydroxy-cyclohexyl-phenyl-ketone, 2-methyl-1-(4-methylthiophenyl)-2-morpholinopropan-1-one, bis(2,4,6-trimethylbenzoyl)-phenylphosphine oxide, phenylglyoxylic acid methyl ester, 1,2-octanedione, 1-[4-(phenylthio)-, 2-(O-benzoyl oxime)], and triarylsulfonium hexafluorophosphate. Examples of the thermal polymerization initiator include azobisisobutyronitrile and benzoyl peroxide. The content of the polymerization initiator is preferably 0.01 parts by weight or more and 1 part by weight or less relative to 100 parts by weight of the liquid monomer mixture before polymerization minus the polymerization initiator, though not limited thereto. In the case of polymerization by UV irradiation, the integrated dose of UV radiation is, for example, preferably in the range of 1000 $mJ/cm^2$ to 10000 $mJ/cm^2$, more preferably in the range of 2000 $mJ/cm^2$ to 10000 $mJ/cm^2$, though it varies depending on the content of the polymerization initiator. By the method described above, a gel sheet of the present aspect comprising the gel sheet layer A and the gel sheet layer B with desired properties can be obtained.

The above descriptions of the first to third embodiments of the gel sheet of the present invention can be replaced with and applied to each other. For example, the description on the composition of the gel material, the structure of the intermediate base, etc., to constitute the gel sheet in any one embodiment of the first to third embodiments may apply to another embodiment of the first to third embodiments in the same manner.

Another aspect of the present invention relates to an electrode pad having a gel sheet of an aspect of the present invention and an electrode electrically connected to the gel sheet layer A or the gel sheet layer B of the gel sheet. The electrode pad of the present aspect can be applied to an electrode part of various equipment including, for example, medical equipment such as measurement equipment for use on a living body or electrotherapeutic equipment for use on a living body, measurement equipment for inspecting the surface of the ground or bedrock, industrial measurement equipment such as equipment for detecting breakage of a water shield sheet used in waste treatment plants and the like. In a preferred embodiment, the electrode pad of the present aspect is an electrode pad for use on a living body in medical equipment such as measurement equipment for use on a living body or electrotherapeutic equipment for use on a living body.

Preferably the electrode pad of the present aspect is for applying a direct current. As described above, the gel sheet of an aspect of the present invention can substantially suppress the increase in pH and the decrease in conductivity even when a direct current is applied for a certain time period. The electrode pad of the present aspect, therefore, can be stably used to apply a direct current for a long period.

Figure 4:
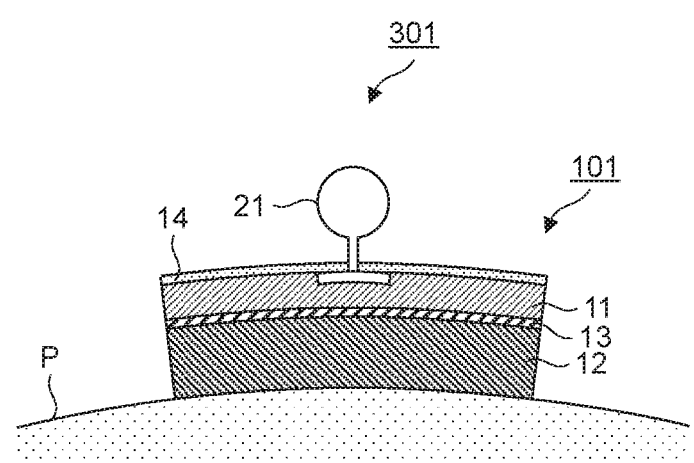
FIG. 4 is a cross-sectional view showing an electrode pad with use of the gel sheet in a first embodiment of the present invention.
Figure 4:
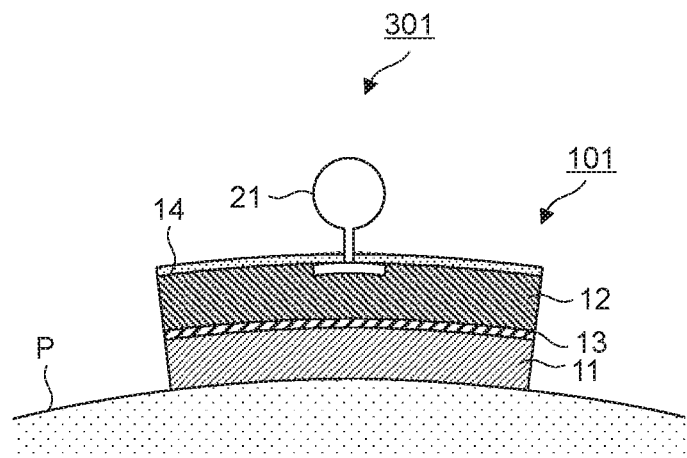

An electrode pad of the present aspect in a first embodiment is shown in FIG. 4. As shown in FIG. 4, an electrode pad 301 of the present aspect comprises a gel sheet 101 of an aspect of the present invention, and an electrode 21 electrically connected to a gel sheet layer A 11 or a gel sheet layer B of a gel sheet. In FIG. 4A, an electrode pad 301 in an embodiment of the present aspect comprising a gel sheet 101 of an aspect of the present invention and an electrode 21 electrically connected to a gel sheet layer A 11 of a gel sheet is shown, and in FIG. 4B, an electrode pad 301 in an embodiment of the present aspect comprising a gel sheet 101 of an aspect of the present invention and an electrode 21 electrically connected to a gel sheet layer B 12 of a gel sheet is shown, respectively. The electrode pad 301 of the present aspect is typically disposed in close contact with a surface P of an adherend. In the electrode pad 301 of the present aspect, the gel sheet layer A 11 or the gel sheet layer B 12 which is not connected to the electrode 21 of the gel sheet 101 is used as a contact part in contact with a surface P of an adherend. The gel sheet layer A 11 and the gel sheet layer B 12 have adhesiveness and flexibility, so that the electrode pad 301 of the present aspect can be brought in close contact with the adherent along the shape of the surface P through the outer surface of the gel sheet layer A 11 or the gel sheet layer B 12.

Figure 5:
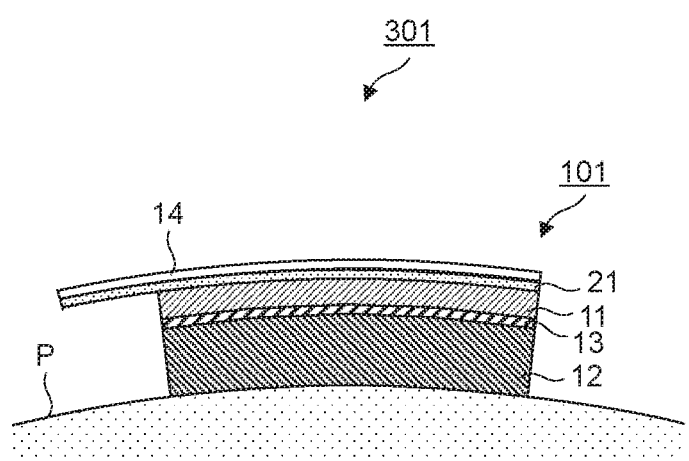
FIG. 5 is a cross-sectional view showing an electrode pad with use of the gel sheet in a second embodiment of the present invention.
Figure 5:
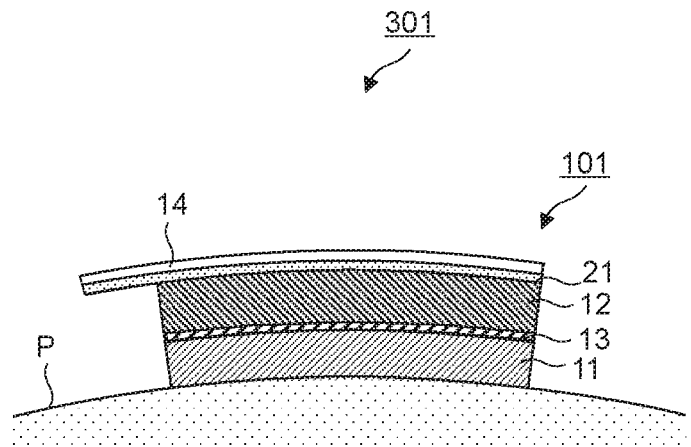

The electrode pad of the present invention in a second embodiment is described based on FIG. 5. As shown in FIG. 5, an electrode pad 301 of the present aspect may comprise an electrode 21 disposed on the surface of a supporting base 14 to be described as follows and a gel sheet 101 of an aspect of the present invention so as to be stacked on the surface of the electrode 21.

For example, in the case where the electrode pad 301 of the present aspect is in an embodiment of an electrode pad for use on a living body, the surface P of an adherend is preferably a part of a living body such as the skin. As described above, the gel sheet 101 of an aspect of the present invention can substantially suppress the increase in pH and the decrease in conductivity even when a direct current is applied for a certain time period. The electrode pad 301 of the present aspect can be, therefore, stably used to apply a direct current for a long period without substantial effect on the surface P of an adherend.

Preferably, the electrode pad 301 of the present aspect may further comprise a supporting base 14 on the outer surface of the gel sheet layer A 11 or the gel sheet layer B 12, if desired. Preferably the supporting base 14 is disposed to cover approximately the whole outer surface of the gel sheet layer A 11 or the gel sheet layer B 12. Since in the electrode pad 301 of the present aspect, the supporting base 14 is disposed, the outer surfaces of the gel sheet layer A 11 or the gel sheet layer B 12 can be insulated and protected from contamination and/or drying, or the like.

As the supporting base 14, a typical insulating resin may be used. Preferably, the supporting base 14 is a film comprising polyester, polyethylene, polypropylene, polyvinyl chloride, PET, polyurethane, or silicone, a foam, a nonwoven fabric, a rubber, or the like.

For example, in an embodiment shown in FIG. 4, preferably the supporting base 14 is a woven or nonwoven fabric, having excellent processability and/or moisture permeability with good adhesiveness to a gel sheet 101. In the present embodiment, a nonwoven fabric made of polyolefin produced by a spun-bonding method is particularly preferred as the supporting base 14 among them. The thickness of the supporting base 14 is not particularly limited, and, for example, in the range of 0.2 to 1.2 mm. With a thickness of the supporting base 14 of less than 0.2 mm, the supporting base 14 is softened, and the shape retention of the electrode pad 301 may be impaired. With a thickness of the supporting base 14 of more than 1.2 mm, the electrode pad 301 cannot be formed into a compact shape due to the excessively thickened supporting base 14, so that the operability may be impaired. The basis weight of the supporting base 14 is, for example, in the range of 50 to 110 $g/m^2$, though not particularly limited. With a basis weight of the supporting base 14 of less than 50 $g/m^2$, the shape retention of the electrode pad 301 may be impaired due to the softened supporting base 14. With a basis weight of the supporting base 14 of more than 110 g/m, the flexibility of the supporting base 14 is impaired, so that the operability of the electrode pad 301 may be impaired.

For example, in an embodiment shown in FIG. 5, preferably the supporting base 14 is a soft film with no elasticity and relatively high stiffness among the ones described above. Examples of the resin film include a resin film of PET, polyvinyl chloride, polyethylene and polypropylene. In the present embodiment, preferably the supporting base 14 is the resin film having a thickness of 10 to 500 μm. Preferably, the supporting base 14 is a PET film, allowing printing to be easily performed with high stiffness, in particular.

The electrode 21 can be typically obtained from a predetermined conductive material. Examples of the conductive material include metals such as nickel, molybdenum, stainless steel, silver and platinum, a metal mixture of silver or silver-silver chloride, and a conductive paste prepared by mixing carbon black, graphite, or the like alone or mixing with two or more of the materials described above. The electrode 21 can be obtained, for example, by printing a conductive paste on the surface of the supporting base 14 described above to form a conductive layer of an electrode. Alternatively, the electrode 21 may be obtained even by forming a laminate of the supporting base 14 described above and a metal foil of silver, aluminum, tin or the like, or a film containing a conductive material described above.

Another aspect of the present invention relates to an electrotherapeutic equipment for use on a living body comprising the electrode pad for use on a living body of an aspect of the present invention and a power supply part electrically connected to the electrode of the electrode pad for use on a living body. In the electrotherapeutic equipment for use on a living body of the present aspect, the gel sheet layer A of the electrode pad for use on a living body is typically disposed adjacent to the positive electrode, and the gel sheet layer B is typically disposed adjacent to the negative electrode.

Preferably, the electrotherapeutic equipment for use on a living body of the present aspect is used to apply a direct current. As described above, the gel sheet of an aspect of the present invention can substantially suppress the increase in pH and the decrease in conductivity even when a direct current is applied for a certain time period. The electrotherapeutic equipment for use on a living body of the present aspect can be, therefore, stably used to apply a direct current for a long period.

As described in detail above, the gel sheet of an aspect of the present invention can substantially suppress the increase in pH and the decrease in conductivity even when a direct current is applied for a certain time. By applying the gel sheet of an aspect of the present invention as a constitutional member of an electrode pad used for an electrode part in various equipment including medical equipment such as measurement equipment for use on a living body or electrotherapeutic equipment for use on a living body, measurement equipment for inspecting the surface of the ground or bedrock, industrial measurement equipment such as equipment for detecting breakage of a water shield sheet used in waste treatment plants and the like, these equipment can be stably used to apply a direct current for a long period, in particular.

Figure 6:
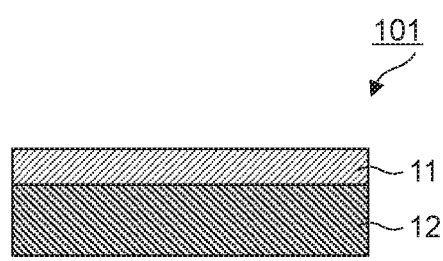
FIG. 6 is a cross-sectional view showing a gel sheet in another embodiment of the present invention in an aspect.
Figure 7:
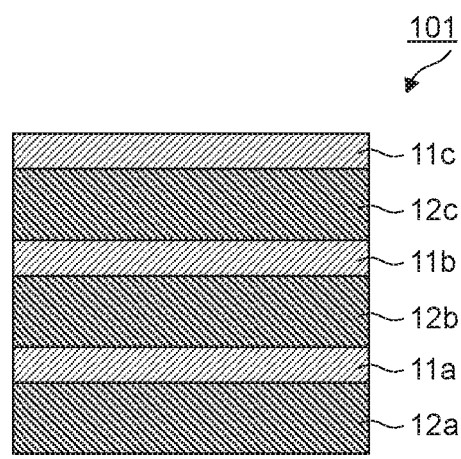
FIG. 7 is a cross-sectional view showing a gel sheet in another embodiment of the present invention in an aspect.

FIGS. 6 and 7 are cross-sectional views showing a gel sheet in another embodiment of the present invention. The embodiments shown in FIGS. 6 and 7 correspond to the gel sheet 101 in the second and third embodiments shown in FIGS. 2 and 3, with the membranes 13, 13a, 13b, 13c, 13ab and 13bc as the intermediate base removed from the gel sheet 101, respectively. The structure and the effect of the gel sheet 101 shown in FIGS. 6 and 7 are the same as in the case of the second and the third embodiments, except that the membrane as the intermediate base is not included.

Figure 8:
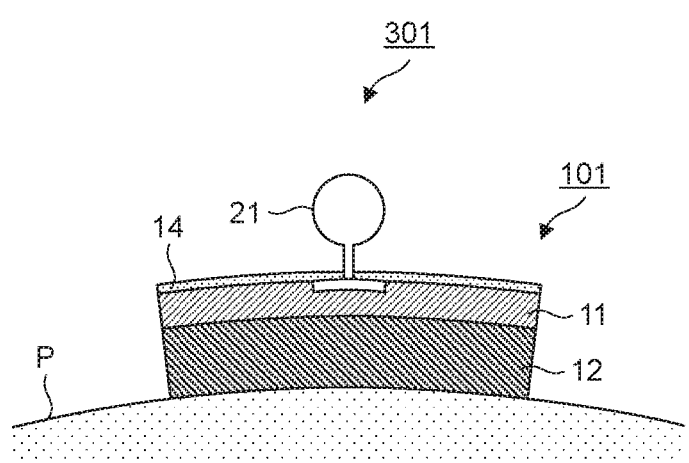
FIG. 8 is a cross-sectional view showing an electrode pad with use of a gel sheet in another embodiment of the present invention in an aspect.
Figure 8:
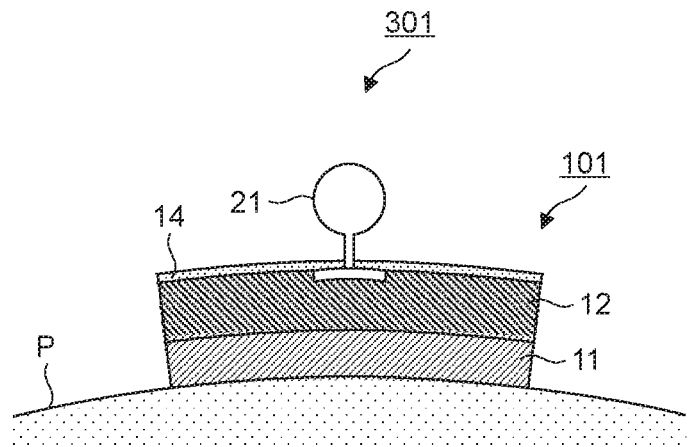
Figure 9:
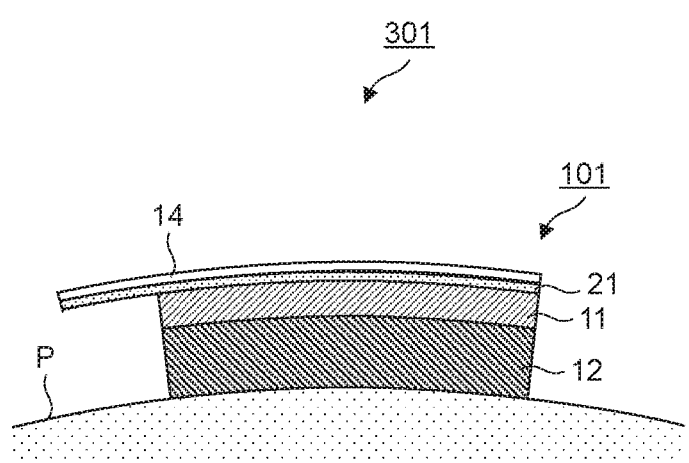
FIG. 9 is a cross-sectional view showing an electrode pad with use of a gel sheet in another embodiment of the present invention in an aspect.
Figure 9:
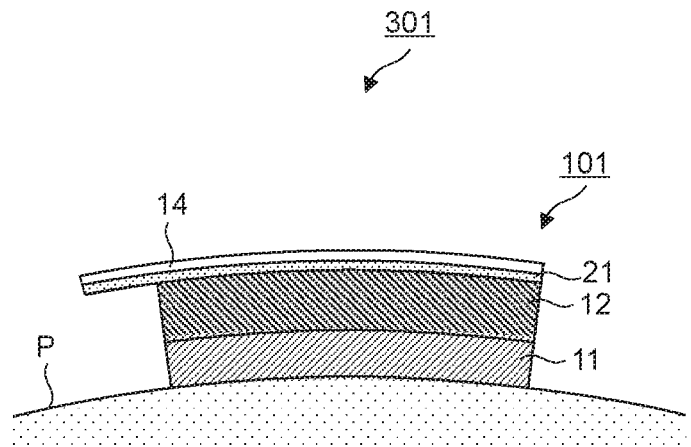

FIGS. 8 and 9 are cross-sectional views showing an electrode pad with use of the gel sheet of the present invention in another embodiment. The embodiments shown in FIGS. 8 and 9 correspond to the electrode pads 301 in the first and second embodiments shown in FIGS. 4 and 5, with the membrane 13 as the intermediate base removed from the electrode pads 310, respectively. The structure and the effect of the electrode pads shown in FIGS. 8 and 9 are equivalent to those in the case of the first and the second embodiments, except that the membrane as the intermediate base is not included.

EXAMPLES

Hereinafter, the present invention is described in more detail based on Examples and Comparative Examples, though the present invention is not limited to these examples.

Example 1

A mixture in an amount of 100 parts by weight was prepared by adding ion exchange water to weighed 20 parts by weight of acrylamide, 0.04 parts by weight of N,N-methylenebisacrylamide, 2 parts by weight of sodium chloride, and 60 parts by weight of glycerol. To the 100 parts by weight of the mixture, 0.13 parts by weight of 2-hydroxy-2-methyl-1-phenyl-propan-1-one (trade name: IRGACURE IR1173) was added as photopolymerization initiator to be mixed and dissolved, so that a liquid monomer mixture was obtained. Subsequently, 10 sheets of silicone film having a thickness of 0.1 mm were stacked, of which central part was cut out to make a 120 mm by 120 mm by 1.0 mm space. In the space, a polyester nonwoven fabric having a thickness of 0.15 mm and a basis weight of 18 $g/m^2$ as intermediate base was placed, with one end on the fifth layer of the silicone films and another end on the fifth layer of the silicone films so as to be inserted, and fixed with an adhesive to prepare a formwork. Subsequently, a small amount of ion exchange water was dropped onto a 150-mm square glass substrate, to which a PET film coated with silicone having a thickness of 100 µm, cut into a 150-mm square, was attached and closely adhered. On the top face of the PET film, the formwork prepared in advance was placed, and the liquid monomer mixture was dropped into the formwork. Furthermore, the top face thereof was covered with a PET film coated with silicone having a thickness of 40 µm, cut into a 150-mm square, and a glass substrate was placed on the top face thereof to be fixed with a clip. Polymerization was performed with a UV irradiation apparatus (JU-C1500 manufactured by JATEC, metal halide lamp, conveyor speed: 0.4 m/min, total irradiation energy: 3000 mJ/cm$^2$) to obtain a gel sheet.

Example 2

A gel sheet was obtained in the same manner as in Example 1, except that one end of the intermediate base was placed on the sixth layer of the silicone films and another end on the fourth layer of the silicone films so as to be inserted.

Example 3

A gel sheet was obtained in the same manner as in Example 1, except that one end of the intermediate base was placed on the sixth layer of the silicone films and another end on the third layer of the silicone films so as to be inserted.

Example 4

A gel sheet was obtained in the same manner as in Example 1, except that one end of the intermediate base was placed on the seventh layer of the silicone films and another end on the third layer of the silicone films so as to be inserted.

Example 5

A gel sheet was obtained in the same manner as in Example 1, except that 6 sheets of silicone film were used in the preparation of the formwork, and using a polyester nonwoven fabric having a thickness of 0.1 mm and a basis weight of 14 g/m$^2$ as the intermediate base, one end of the intermediate base was placed on the fourth layer of the silicone films and another end on the third layer of the silicone films so as to be inserted.

Example 6

A gel sheet was obtained in the same manner as in Example 1, except that using a cellophane sheet having a thickness of 0.03 mm as the intermediate base, one end of the intermediate base was placed on the sixth layer of the silicone films and another end on the fourth layer of the silicone films so as to be inserted.

Example 7

A gel sheet was obtained in the same manner as in Example 1, except that 15 sheets of silicone film were used in the preparation of the formwork, and using a polyester nonwoven fabric having a thickness of 0.67 mm and a basis weight of 70 g/m$^2$ as the intermediate base, one end of the intermediate base was placed on the fifth layer of the silicone films and another end on the tenth layer of the silicone films so as to be inserted.

Comparative Example 1

A gel sheet was obtained in the same manner as in Example 1, except that one end of the intermediate base was placed on the eighth layer of the silicone films and another end on the third layer of the silicone films so as to be inserted.

Comparative Example 2

A gel sheet was obtained in the same manner as in Example 1, except that 6 sheets of silicone film were used in the preparation of the formwork, and using a polyester nonwoven fabric having a thickness of 0.1 mm and a basis weight of 14 g/m$^2$ as the intermediate base, one end of the intermediate base was placed on the fifth layer of the silicone films and another end on the second layer of the silicone films so as to be inserted.

Comparative Example 3

A gel sheet was obtained in the same manner as in Example 1, except that one end of the intermediate base was placed on the eighth layer of the silicone films and another end on the first layer of the silicone films so as to be inserted.
(Evaluation on Adhesive Force of Gel Sheet)

A gel sheet was cut into dimensions of 120 mm by 20 mm, and the PET film having a thickness of 100 µm was peeled off to expose a gel surface, to which a Bakelite plate was attached and pressure bonded with a 2-kg pressure bonding roller in a reciprocating cycle, so that a test piece was prepared. A rheometer (CR-500DX, manufactured by Sun Scientific Co., Ltd.) was used in the measurement under measurement conditions at an angle of 90 degrees and a speed of 300 mm/minute. The stress values (N/20 mm) at a predetermined peeling point (30, 40, 50, 60 and 70 mm) from a measurement starting point were defined as the measurement values. Based on the values obtained by testing three times (15 points in total), a coefficient of variation, i.e., CV value, was calculated from the following expression, to define as an index of the variation of the adhesive force of the gel sheet.

CV value (%)=(standard deviation×100)/average value

The measurement was performed under environment at a temperature of 23±5° C., at a humidity of 55° %±10%.
(Measurement of Amplitude of Intermediate Base)

A gel sheet was cut into sizes of 50 mm by 20 mm with a razor, and the cross section thereof was observed by a microscope (VH-Z100R manufactured by Keyence Corporation) at three points including the center and both ends across a width of 50 mm, with a magnification of 100. In each of the observation screen (corresponding to a width of 3 mm), the maximum and minimum distances from the end face of the 100-µm PET film to the intermediate base were measured to calculate the difference, and the average value of the calculated differences at the three points was regarded as the amplitude of the intermediate base.
(Measurement of Thickness of Gel Sheet)

The PET films bonded to both surfaces of a gel sheet were peeled off for the measurement by a micrometer.

The measurement results are summarized and shown in Table 1. As is apparent from the results of Table 1, through control of the ratio (S/T) of the amplitude S of an intermediate base to the thickness T of a gel sheet at 0.4 or less, the variation in the adhesiveness (CV value) was reduced.

obtained in the same manner as in Production Example 1, except that the amount of sodium chloride in the liquid monomer mixture was changed to 0 part by weight and the thickness of the formwork of silicone rubber sheet was changed to 0.6 mm in Production Example 1.

TABLE 1

|  | Example | | | | | | | Comparative Example | | |
| --- | --- | --- | --- | --- | --- | --- | --- | --- | --- | --- |
|  | 1 | 2 | 3 | 4 | 5 | 6 | 7 | 1 | 2 | 3 |
| Thickness of gel sheet T [mm] | 1.0 | 1.0 | 1.0 | 1.0 | 0.6 | 1.0 | 1.5 | 1.0 | 0.6 | 1.0 |
| Amplitude S [mm] | 0 | 0.2 | 0.3 | 0.4 | 0.1 | 0.2 | 0.5 | 0.5 | 0.3 | 0.7 |
| Type of intermediate base | Polyester nonwoven fabric | ← | ← | ← | ← | Cellophane | Polyester nonwoven fabric | Polyester nonwoven fabric | ← | ← |
| S/T | 0 | 0.20 | 0.30 | 0.40 | 0.17 | 0.20 | 0.33 | 0.50 | 0.50 | 0.70 |
| Thickness of intermediate base [mm] | 0.15 | 0.15 | 0.15 | 0.15 | 0.1 | 0.03 | 0.67 | 0.15 | 0.1 | 0.15 |
| CV value [%] | 4.3 | 5.4 | 6.1 | 8.1 | 6.3 | 5.1 | 7.2 | 15.1 | 17.3 | 21.3 |

<I. Production of Gel Sheet Layer to Constitute Gel Sheet>

Production Example 1: Production of Gel Sheet Layer Containing a Large Amount of Inorganic Salt A mixture in the total amount of 100 parts by weight was obtained by adding glycerol to weighed 20 parts by weight of acrylamide, 0.03 parts by weight of N,N-methylenebisacrylamide, 5 parts by weight of sodium chloride, 28 parts by weight of ion exchange water, 1 part by weight of citric acid, and 2 parts by weight of trisodium citrate. To the mixture in an amount of 100 parts by weight, 0.13 parts by weight of 2-hydroxy-2-methyl-1-phenyl-propan-1-one (trade name: IRGACURE IR1173) was added as photopolymerization initiator to be mixed and dissolved, so that a liquid monomer mixture was obtained. Subsequently, a silicone rubber sheet having a thickness of 0.3 mm was cut out to prepare a formwork having a 120 mm by 120 mm space. Subsequently, a small amount of ion exchange water was dropped onto a 150-mm square glass substrate, to which a PET film coated with silicone having a thickness of 100 μm, cut into a 150-mm square, was attached and closely adhered. On the top face of the PET film, the formwork of silicone rubber sheet prepared in advance was placed. The liquid monomer mixture was dropped into the formwork. Furthermore, the top face thereof was covered with a PET film coated with silicone having a thickness of 40 μm, cut into a 150-mm square. A glass substrate was placed on the top face of the PET film to be fixed with a clip. The assembly was exposed to UV radiation with a UV irradiation apparatus (JU-C1500 manufactured by JATEC, metal halide lamp, conveyor speed: 0.4 m/min, total irradiation energy: 3000 mJ/cm$^2$). The monomers were polymerized by UV irradiation to produce a gel sheet layer having a film thickness of 0.3 mm, containing 5 wt % of sodium chloride as an inorganic salt, 1 wt % of citric acid as an acid, and 28 wt % of water relative to the total weight of the gel sheet layer.

Production Example 2: Production of Gel Sheet Layer not Containing Inorganic Salt A gel sheet layer having a film thickness of 0.6 mm, containing 1 wt % of citric acid as an acid and 28 wt % of water, not containing sodium chloride as an inorganic salt, relative to the total weight of the gel sheet layer, was obtained in the same manner as in Production Example 1, except that the amount of sodium chloride in the liquid monomer mixture was changed to 0 part by weight and the thickness of the formwork of silicone rubber sheet was changed to 0.6 mm in Production Example 1.

Production Example 3: Production of Gel Sheet Layer Containing a Large Amount of Inorganic Salt A gel sheet layer having a film thickness of 0.6 mm, containing 5 wt % of sodium chloride as an inorganic salt, 1 wt %6 of citric acid as an acid, and 28 wt % of water relative to the total weight of the gel sheet layer, was obtained in the same manner as in Production Example 1, except that the thickness of the formwork of silicone rubber sheet was changed to 0.6 mm in Production Example 1.

Production Example 4: Production of Gel Sheet Layer not Containing Inorganic Salt A gel sheet layer having a film thickness of 0.3 mm, containing 1 wt % of citric acid as an acid and 28 wt of water, not containing sodium chloride as an inorganic salt, relative to the total weight of the gel sheet layer, was obtained in the same manner as in Production Example 1, except that the amount of sodium chloride in the liquid monomer mixture was changed to 0 part by weight and the thickness of the formwork of silicone rubber sheet was changed to 0.3 mm in Production Example 1.

Production Example 5: Production of Gel Sheet Layer not Containing Inorganic Salt A gel sheet layer having a film thickness of 0.9 mm, containing 1 wt/o of citric acid as an acid and 28 wt % of water, not containing sodium chloride as an inorganic salt, relative to the total weight of the gel sheet layer, was obtained in the same manner as in Production Example 1, except that the amount of sodium chloride in the liquid monomer mixture was changed to 0 part by weight and the thickness of the formwork of silicone rubber sheet was changed to 0.9 mm in Production Example 1.

Production Example 6: Production of Gel Sheet Layer not Containing Inorganic Salt A gel sheet layer having a film thickness of 0.6 mm, containing 1 wt % of tartaric acid as an acid and 28 Wt %/o of water, not containing sodium chloride as an inorganic salt, relative to the total weight of the gel sheet layer, was obtained in the same manner as in Production Example 1, except that the amount of sodium chloride in the liquid monomer mixture was changed to 0 part by weight and the thickness of the formwork of silicone rubber sheet was changed to 0.6 mm in Production Example 1.

Production Example 7: Production of Gel Sheet Layer not Containing Inorganic Salt A gel sheet layer having a film thickness of 0.6 mm, containing 1 wt % of citric acid as an acid and 38 wt % of water, not containing sodium chloride as an inorganic salt, relative to the total weight of the gel sheet layer, was obtained in the same manner as in Production Example 1, except that the amount of sodium chloride in the liquid monomer mixture was changed to 0 part by weight and the thickness of the formwork of silicone rubber sheet was changed to 0.6 mm in Production Example 1.

Production Example 8: Production of Gel Sheet Layer Containing a Large Amount of Inorganic Salt A gel sheet layer having a film thickness of 0.6 mm, containing 5 wt % of sodium sulfate as an inorganic salt, 1 wt % of citric acid as an acid, and 28 wt % of water relative to the total weight of the gel sheet layer, was obtained in the same manner as in Production Example 1, except that the thickness of the formwork of silicone rubber sheet was changed to 0.6 mm and the inorganic salt was replaced with 5 wt % of sodium sulfate in Production Example 1.

Production Example 9: Production of Gel Sheet Layer Containing a Large Amount of Inorganic Salt A gel sheet layer having a film thickness of 0.9 mm, containing 5 wt % of sodium chloride as an inorganic salt, 1 wt % of citric acid as an acid, and 28 wt % of water relative to the total weight of the gel sheet layer, was obtained in the same manner as in Production Example 1, except that the thickness of the formwork of silicone rubber sheet was changed to 0.9 mm in Production Example 1.

Production Example 10: Production of Gel Sheet Layer Containing a Small Amount of Inorganic Salt A gel sheet layer having a film thickness of 0.3 mm, containing 0.5 wt % of sodium chloride as an inorganic salt, 1 wt % of citric acid as an acid, and 28 wt % of water relative to the total weight of the gel sheet layer, was obtained in the same manner as in Production Example 1, except that the amount of sodium chloride in the liquid monomer mixture was changed to 0.5 parts by weight in Production Example 1.

Production Example 11: Production of Gel Sheet Layer Containing a Large Amount of Inorganic Salt A gel sheet layer having a film thickness of 0.3 mm, containing 2.5 wt % of sodium chloride as an inorganic salt, 1 wt % of citric acid as an acid, and 28 wt % of water relative to the total weight of the gel sheet layer, was obtained in the same manner as in Production Example 1, except that the amount of sodium chloride in the liquid monomer mixture was changed to 2.5 parts by weight in Production Example 1.

Production Example 12: Production of Gel Sheet Layer Containing a Large Amount of Inorganic Salt A gel sheet layer having a film thickness of 0.6 mm, containing 2.5 wt % of sodium chloride as an inorganic salt, 1 wt % of citric acid as an acid, and 28 wt % of water relative to the total weight of the gel sheet layer, was obtained in the same manner as in Production Example 1, except that the amount of sodium chloride in the liquid monomer mixture was changed to 2.5 parts by weight and the thickness of the formwork of silicone rubber sheet was changed to 0.6 mm in Production Example 1.

Production Example 13: Production of Gel Sheet Layer not Containing Inorganic Salt A gel sheet layer having a film thickness of 0.6 mm, containing 28 wt % of water relative to the total weight of the gel sheet layer, not containing any one of sodium chloride as an inorganic salt and citric acid as an acid, was obtained in the same manner as in Production Example 1, except that the amount of sodium chloride was changed to 0 part by weight, the amount of citric acid to 0 part by weight in the liquid monomer mixture, and the thickness of the formwork of silicone rubber sheet was changed to 0.6 mm in Production Example 1.

<II. Production of Gel Sheet Comprising a Plurality of Gel Sheet Layers Stacked>

Example 8

A gel sheet layer prepared in Production Example 1, having a film thickness of 0.3 mm, containing a large amount of inorganic salt, and a gel sheet layer prepared in Production Example 2, having a film thickness of 0.6 mm, not containing any inorganic salt were stacked, and a semipermeable membrane of cellophane (FP-300, manufactured by Futamura Chemical Co., Ltd.) as an intermediate base was further disposed therebetween, so that a gel sheet having a total film thickness of 0.93 mm was obtained. In the gel sheet thus obtained, the gel sheet layer containing a large amount of inorganic salt corresponds to a gel sheet layer A, and the gel sheet layer not containing inorganic salt corresponds to a gel sheet layer B, respectively. In the present Example, the gel sheet layer A is disposed on the top face of the gel sheet layer B.

Example 9

A gel sheet having a total film thickness of 0.93 mm was obtained in the same manner as in Example 8, except that the gel sheet layer A was replaced with the gel sheet layer prepared in Production Example 3, having a film thickness of 0.6 mm, containing a large amount of inorganic salt, and the gel sheet layer B was replaced with the gel sheet layer prepared in Production Example 4, having a film thickness of 0.3 mm, in Example 8.

Example 10

A gel sheet having a total film thickness of 1.23 mm was obtained in the same manner as in Example 8, except that the gel sheet layer B was replaced with the gel sheet layer prepared in Production Example 5, having a film thickness of 0.9 mm, not containing inorganic salt, in Example 8.

Example 11

A gel sheet having a total film thickness of 0.93 mm was obtained in the same manner as in Example 8, except that the gel sheet layer B was replaced with the gel sheet layer prepared in Production Example 6, having a film thickness of 0.6 mm, not containing inorganic salt, in Example 8.

Example 12

A gel sheet having a total film thickness of 0.93 mm was obtained in the same manner as in Example 8, except that the gel sheet layer B was replaced with the gel sheet layer prepared in Production Example 7, having a film thickness of 0.6 mm, not containing inorganic salt, in Example 8.

Example 13

The gel sheet layer prepared in Production Example 1, having a film thickness of 0.3 mm, containing a large amount of inorganic salt, and the gel sheet layer prepared in Production Example 2, having a film thickness of 0.6 mm, not containing inorganic salt were stacked, and a polyester nonwoven fabric having a thickness of 0.15 mm and a basis weight of 18 g/m$^2$ was further disposed therebetween as an intermediate base, so that a gel sheet having a total film thickness of 1.05 mm was obtained.

Example 14

A gel sheet having a total film thickness of 1.23 mm was obtained in the same manner as in Example 8, except that the gel sheet layer A was replaced with the gel sheet layer prepared in Production Example 8, having a film thickness of 0.6 mm, containing a large amount of inorganic salt, in Example 8.

Example 15

Two of the gel sheet layers prepared in Production Example 1, having a film thickness of 0.3 mm, containing a large amount of inorganic salt, and two of the gel sheet layers prepared in Production Example 2, having a film thickness of 0.6 mm, not containing inorganic salt were alternately stacked, so that a gel sheet having a total film thickness of 1.83 mm was obtained. In the gel sheet thus obtained, the two gel sheet layers containing a large amount of inorganic salt correspond to gel sheet layers A (hereinafter also referred to as "gel sheet layer A" and "gel sheet layer A'"), and the two gel sheet layers not containing inorganic salt correspond to gel sheet layers B (hereinafter also referred to as "gel sheet layer B" and "gel sheet layer B'"), respectively. Between the gel sheet layer A and the gel sheet layer B', a semipermeable membrane of cellophane (FP-300, manufactured by Futamura Chemical Co., Ltd.) was disposed as an intermediate base. In the present Example, on the top face of the gel sheet layer B, the gel sheet layer A is disposed; on the top face of the gel sheet layer A, the gel sheet layer B' is disposed; and on the top face of the gel sheet layer B', the gel sheet layer A' is disposed.

Example 16

A gel sheet having a total film thickness of 1.83 mm was obtained in the same manner as in Example 8, except that the gel sheet layer A was replaced with the gel sheet layer prepared in Production Example 9, having a film thickness of 0.9 mm, containing a large amount of inorganic salt, and the gel sheet layer B was replaced with the gel sheet layer prepared in Production Example 5, having a film thickness of 0.9 mm, in Example 8.

Example 17

A gel sheet having a total film thickness of 0.93 mm was obtained in the same manner as in Example 8, except that the gel sheet layer A was replaced with the gel sheet layer prepared in Production Example 2, having a film thickness of 0.6 mm, not containing inorganic salt, and the gel sheet layer B was replaced with the gel sheet layer prepared in Production Example 10, having a film thickness of 0.3 mm, containing a small amount of inorganic salt, respectively, in Example 8.

Example 18

A gel sheet having a total film thickness of 0.93 mm was obtained in the same manner as in Example 1, except that the gel sheet layer A was replaced with the gel sheet layer prepared in Production Example 11, having a film thickness of 0.3 mm, containing a large amount of inorganic salt, and the gel sheet layer B was replaced with the gel sheet layer prepared in Production Example 12, having a film thickness of 0.6 mm, containing a large amount of inorganic salt, respectively, in Example 8.

Example 19

A gel sheet having a total film thickness of 0.93 mm was obtained in the same manner as in Example 8, except that the gel sheet layer B was replaced with the gel sheet layer prepared in Production Example 13, having a film thickness of 0.6 mm, not containing inorganic salt, in Example 8.

Example 20

A gel sheet having a total film thickness of 0.93 mm was obtained in the same manner as in Example 8, except that the gel sheet layer A was replaced with the gel sheet layer prepared in Production Example 4, having a film thickness of 0.3 mm, not containing inorganic salt, in Example 8.

<III: Evaluation of Gel Sheet>

[III-1: Change in Resistance Value for Direct Current Application]

Two sets each of the test materials of gel sheet in Examples 8 to 20 cut into 25-mm squares, held between two SUS plates, respectively, were prepared. To the SUS plate adjacent to the gel sheet layer A (Examples 8 to 14 and 16 to 20) or the gel sheet layer A' (Example 15) of one of the test materials of the two sets, the positive electrode of a stabilized DC power supply (PAR 18-6A, manufactured by TEXIO) was connected, and to the SUS plate adjacent to the gel sheet layer B of the other test material, the negative electrode was connected, respectively. Of the two sets of the test materials, between one SUS plate adjacent to the gel sheet layer B not connected to any of the positive electrode or the negative electrode and another SUS plate adjacent to the gel sheet layer A (Examples 8 to 14 and 16 to 20) or the gel sheet layer A' (Example 15), a resistance of 1 kΩ was connected. In the circuit, the resistance simulates the surface of an adherend such as the skin of a living body. To the circuit, a direct current was applied under application conditions with an applied DC voltage of 3V for an application time of 10 minutes. Based on the measured resistance of the circuit, the test material with no change in resistance was rated as good, and the test material with increased resistance was rated as fair.

[III-2: Change in pH for Direct Current Application]

In the same manner as described in III-1, a direct current was applied to a circuit connected to each of the test materials of gel sheets in Examples 8 to 20. After the application, the gel sheet was removed from the test material. A pH test paper was placed on the surface of the gel sheet layer B of each of the gel sheets in Examples 8 to 20. Both of the surfaces of the gel sheet were held between PET films to keep for 1 minute. The pH test paper was then taken out to confirm the pH value. The pH value of the gel sheet layer B of each of the gel sheets in Examples 8 to 20 before application of the direct current was measured in the same manner. As a result, any of the gel sheets in Examples 8 to 20 had a pH of 5. Based on the pH before application of the direct current, the gel sheet with a pH value after application in the range of 3 to 8 was rated as good, and in the range of 2 or less, or 9 or more as fair.

[III-3: Evaluation on Adhesive Force of Gel Sheet]

In the same manner as described in III-1, a direct current was applied to a circuit connected to each of the test materials of gel sheets in Examples 8 to 20. After the application, the gel sheet was removed from the test material. The coefficients of variation, i.e., CV values of the gel sheets before and after application were calculated in the same manner as in Examples 1 to 7 and Comparative Examples 1 to 3, to define as the indices of variation in the adhesive force of the gel sheet.

[III-4: Evaluation Results]

Of the gel sheets in Examples 8 to 20 each, the dimensions and the amount of inorganic salt of the gel sheet layer, and the evaluation results with direct current applied to the gel sheet are shown in Table 2. It is noted that the thickness T of a gel sheet and the amplitude S of an intermediate base in Table 2 were measured in the same manner as in Examples 1 to 7 and Comparative Examples 1 to 3.

TABLE 2

|  |  | Example | | | | | |
| --- | --- | --- | --- | --- | --- | --- | --- |
|  |  | 8 | 9 | 10 | 11 | 12 | 13 |
| Layer A | Thickness a [mm] | 0.3 | 0.6 | 0.3 | 0.3 | 0.3 | 0.3 |
|  | Salt concentration X [wt %] | 5.0 | 5.0 | 5.0 | 5.0 | 5.0 | 5.0 |
| Layer B | Thickness b [mm] | 0.6 | 0.3 | 0.9 | 0.6 | 0.6 | 0.6 |
|  | Salt concentration Y [wt %] | 0 | 0 | 0 | 0 | 0 | 0 |
|  | Amount of acid [wt %] | 1 | 1 | 1 | 1 (Tartaric acid) | 1 | 1 |
|  | Water content α [wt %] | 28 | 28 | 28 | 28 | 38 | 28 |
|  | Y/α | 0 | 0 | 0 | 0 | 0 | 0 |
|  | Thickness of gel sheet T [mm] | 0.93 | 0.93 | 1.23 | 0.93 | 0.93 | 1.05 |
|  | Type of intermediate base (thickness [mm]) | Cellophane (0.03) | ← (0.03) | ← (0.03) | ← (0.03) | ← (0.03) | Polyester nonwoven fabric (0.15) |
|  | Amplitude S [mm] | 0 | 0 | 0 | 0 | 0.1 | 0.15 |
|  | X > Y | Good | Good | Good | Good | Good | Good |
|  | b/a ≥ 1 | Good | Poor | Good | Good | Good | Good |
|  | S/T | 0 | 0 | 0 | 0 | 0.11 | 0.14 |
|  | Resistance | Good | Good | Good | Good | Good | Good |
|  | pH of layer B after application | Good (5) | Fair (9) | Good (5) | Good (5) | Good (5) | Good (7) |
|  | CV value (before application) | 4.0 | 5.2 | 4.2 | 4.2 | 5.3 | 5.1 |
|  | CV value (after application) | 9.2 | 10.1 | 9.5 | 9.3 | 9.9 | 9.1 |

|  |  | Example | | | | | | |
| --- | --- | --- | --- | --- | --- | --- | --- | --- |
|  |  | 14 | 15 | 16 | 17 | 18 | 19 | 20 |
| Layer A | Thickness a [mm] | 0.6 | 0.3 | 0.9 | 0.6 | 0.3 | 0.3 | 0.3 |
|  | Salt concentration X [wt %] | 5.0 (Na sulfate) | 5.0 | 5.0 | 0 | 2.5 | 5.0 | 0 |
| Layer B | Thickness b [mm] | 0.6 | 0.6 | 0.9 | 0.3 | 0.6 | 0.6 | 0.6 |
|  | Salt concentration Y [wt %] | 0 | 0 | 0 | 0.5 | 2.5 | 0 | 0 |
|  | Amount of acid [wt %] | 1 | 1 | 1 | 1 | 1 | 0 | 1 |
|  | Water content α [wt %] | 28 | 28 | 28 | 28 | 28 | 28 | 28 |
|  | Y/α | 0 | 0 | 0 | 0.018 | 0.089 | 0 | 0 |
|  | Thickness of gel sheet T [mm] | 1.23 | 1.83 | 1.83 | 0.93 | 0.93 | 0.93 | 0.93 |
|  | Type of intermediate base (thickness [mm]) | Cellophane (0.03) | ← (0.03) | ← (0.03) | ← (0.03) | ← (0.03) | ← (0.03) | ← (0.03) |
|  | Amplitude S [mm] | 0.1 | 0 | 0.1 | 0.1 | 0.1 | 0.15 | 0 |
|  | X > Y | Good | Good | Good | Poor | Poor | Good | Poor |
|  | b/a ≥ 1 | Good | Good | Good | Poor | Good | Good | Good |
|  | S/T | 0.11 | 0 | 0.06 | 0.11 | 0.11 | 0.17 | 0 |
|  | Resistance | Good | Good | Good | Good | Good | Good | Fair |
|  | pH of layer B after application | Good (5) | Good (5) | Good (5) | Fair (9) | Fair (9) | Fair (9) | Good (7) |
|  | CV value (before application) | 4.1 | 4.6 | 4.8 | 8.2 | 7.9 | 8.3 | 4.5 |
|  | CV value (after application) | 9.4 | 9.9 | 9.6 | 16.5 | 17.5 | 18.9 | 13.5 |

As shown in Table 2, each of the gel sheets in Examples 8 and 10 to 16 had no change in the resistance value, with a pH value of the gel sheet layer B unchanged or in the range of 5 to 8, after application of direct current under the conditions described above. In contrast, each of the gel sheets in Examples 9 and 17 to 19 had no change in the resistance value, but the pH value of the gel sheet layer B increased to 9, after application of direct current under the conditions described above. Also, the gel sheet in Example 20 had an increased resistance value, though the pH value of the gel sheet layer B remained at 7, after application of direct current under the conditions described above.

The change in pH of the gel sheets in Example 8, 10 to 12 and 14 to 16 was evaluated in the same manner as described above after 7 days from the preparation of the gel sheets, and it was found that pH was maintained at 5. From the results, it was proved that the disposition of a membrane as intermediate base between the gel sheet layer A and the gel sheet layer B enables the effect of the present invention to be exhibited for a longer period.

In particular, the gel sheet comprising four gel sheet layers in Example 15 further suppresses material transfer between the gel sheet layers, so that the pH did not change from 5 even after 10 days.

Also, through control of the ratio (ST) of the amplitude S of the intermediate base to the thickness T of a gel sheet at 0.4 or less, any of the gel sheets had a small variation (CV value) in the adhesiveness before application.

Then, a plurality of gel sheet layers were stacked to prepare a gel sheet having no intermediate base embedded as a reference example, which was subjected to evaluation on the resistance value and the pH after application in the same manner as in Examples described above.

<I: Production of Gel Sheet>

Reference Production Example 1: Production of Gel Sheet Layer Containing a Large Amount of Inorganic Salt A mixture in the total amount of 100 parts by weight was obtained by adding glycerol to weighed 20 parts by weight of acrylamide, 0.03 parts by weight of N,N-methylenebisacrylamide, 5 parts by weight of sodium chloride, 28 parts by weight of ion exchange water, 1 part by weight of citric acid, and 2 parts by weight of trisodium citrate. To the mixture in an amount of 100 parts by weight, 0.13 parts by weight of 2-hydroxy-2-methyl-1-phenyl-propan-1-one (trade name: IRGACURE IR1173) was added as photopolymerization initiator to be mixed and dissolved, so that a liquid monomer mixture was obtained. Subsequently, a silicone rubber sheet having a thickness of 0.3 mm was cut out to prepare a formwork having a 120 mm by 120 mm space. Subsequently, a small amount of ion exchange water was dropped onto a 150-mm square glass substrate, to which a PET film coated with silicone having a thickness of 100 μm, cut into a 150-mm square, was attached and closely adhered. On the top face of the PET film, the formwork of silicone rubber sheet prepared in advance was placed. The liquid monomer mixture was dropped into the formwork. Furthermore, the top face thereof was covered with a PET film coated with silicone having a thickness of 40 μm, cut into a 150-mm square. A glass substrate was placed on the top face of the PET film to be fixed with a clip. The assembly was exposed to UV radiation with a UV irradiation apparatus (JU-C1500 manufactured by JATEC, metal halide lamp, conveyor speed: 0.4 m/min, total irradiation energy: 3000 mJ/cm$^2$). The monomers were polymerized by UV irradiation to produce a gel sheet layer having a film thickness of 0.3 mm, containing 5 wt % of sodium chloride as an inorganic salt, 1 wt % of citric acid as an acid, and 28 wt % of water relative to the total weight of the gel sheet layer.

Reference Production Example 2: Production of Gel Sheet Layer not Containing Inorganic Salt A gel sheet layer having a film thickness of 0.6 mm, containing 1 wt % of citric acid as an acid and 28 wt ° of water, not containing sodium chloride as an inorganic salt, relative to the total weight of the gel sheet layer, was obtained in the same manner as in Reference Production Example 1, except that the amount of sodium chloride in the liquid monomer mixture was changed to 0 part by weight and the thickness of the formwork of silicone rubber sheet was changed to 0.6 mm in Reference Production Example 1.

Reference Production Example 3: Production of Gel Sheet Layer not Containing Inorganic Salt A gel sheet layer having a film thickness of 0.9 mm, containing 1 wt % of citric acid as an acid and 28 wt %6 of water, not containing sodium chloride as an inorganic salt, relative to the total weight of the gel sheet layer, was obtained in the same manner as in Reference Production Example 1, except that the amount of sodium chloride in the liquid monomer mixture was changed to 0 part by weight and the thickness of the formwork of silicone rubber sheet was changed to 0.9 mm in Reference Production Example 1.

Reference Production Example 4: Production of Gel Sheet Layer not Containing Inorganic Salt A gel sheet layer having a film thickness of 0.3 mm, containing 1 wt % of citric acid as an acid, and 28 wt % of water relative to the total weight of the gel sheet layer, not containing sodium chloride as an inorganic salt, was obtained in the same manner as in Reference Production Example 1, except that the amount of sodium chloride in the liquid monomer mixture was changed to 0 part by weight in Reference Production Example 1.

Reference Production Example 5: Production of Gel Sheet Layer Containing a Large Amount of Inorganic Salt A gel sheet layer having a film thickness of 0.6 mm, containing 5 wt % of sodium chloride as an inorganic salt, 1 wt % of citric acid as an acid, and 28 wt/o of water relative to the total weight of the gel sheet layer, was obtained in the same manner as in Reference Production Example 1, except that the thickness of the formwork of silicone rubber sheet was changed to 0.6 mm in Reference Production Example 1.

Reference Production Example 6: Production of Gel Sheet Layer Containing a Large Amount of Inorganic Salt A gel sheet layer having a film thickness of 0.9 mm, containing 5 wt % of sodium chloride as an inorganic salt, 1 wt % of citric acid as an acid, and 28 wt % of water relative to the total weight of the gel sheet layer, was obtained in the same manner as in Reference Production Example 1, except that the thickness of the formwork of silicone rubber sheet was changed to 0.9 mm in Reference Production Example 1.

Reference Production Example 7: Production of Gel Sheet Layer Containing a Large Amount of Inorganic Salt A gel sheet layer having a film thickness of 0.3 mm, containing 2.5 wt % of sodium chloride as an inorganic salt, 1 wt % of citric acid as an acid, and 28 wt %° of water relative to the total weight of the gel sheet layer, was obtained in the same manner as in Reference Production Example 1, except that the amount of sodium chloride in the liquid monomer mixture was changed to 2.5 parts by weight in Reference Production Example 1.

Reference Production Example 8: Production of Gel Sheet Layer Containing a Large Amount of Inorganic Salt A gel sheet layer having a film thickness of 0.6 mm, containing 2.5 wt % of sodium chloride as an inorganic salt, 1 wt % of citric acid as an acid, and 28 wt % of water relative to the total weight of the gel sheet layer, was obtained in the same manner as in Reference Production Example 1, except that the amount of sodium chloride in the liquid monomer mixture was changed to 2.5 parts by weight and the thickness of the formwork of silicone rubber sheet was changed to 0.6 mm in Reference Production Example 1.

Reference Production Example 9: Production of Gel Sheet Layer Containing a Small Amount of Inorganic Salt A gel sheet layer having a film thickness of 0.6 mm, containing 0.1 wt % of sodium chloride as an inorganic salt, 1 wt % of citric acid as an acid, and 28 wt % of water relative to the total weight of the gel sheet layer, was obtained in the same manner as in Reference Production Example 1, except that the amount of sodium chloride in the liquid monomer mixture was changed to 0.1 parts by weight and the thickness of the formwork of silicone rubber sheet was changed to 0.6 mm in Reference Production Example 1.

Reference Production Example 10: Production of Gel Sheet Layer Containing a Small Amount of Inorganic Salt A gel sheet layer having a film thickness of 0.6 mm, containing 0.1 wt % of sodium chloride as an inorganic salt, 1 wt % of citric acid as an acid, and 38 wt % of water relative to the total weight of the gel sheet layer, was obtained in the same manner as in Reference Production Example 1, except that the amount of sodium chloride was changed to 0.1 parts by weight, the amount of ion exchange water to 38 parts by weight in the liquid monomer mixture, and the thickness of the formwork of silicone rubber sheet was changed to 0.6 mm in Reference Production Example 1.

Reference Production Example 11: Production of Gel Sheet Layer Containing a Small Amount of Inorganic Salt A gel sheet layer having a film thickness of 0.6 mm, containing 0.5 wt % of sodium sulfate as an inorganic salt, 1 wt % of citric acid as an acid, and 50 wt % of water relative to the total weight of the gel sheet layer, was obtained in the same manner as in Reference Production Example 1, except that the amount of 5 parts by weight of sodium chloride was replaced with the amount of 0.5 parts by weight of sodium sulfate and the amount of ion exchange water was changed to 50 parts by weight in the liquid monomer mixture, and the thickness of the formwork of silicone rubber sheet was changed to 0.6 mm in Reference Production Example 1.

Reference Production Example 12: Production of Gel Sheet Layer Containing a Small Amount of Inorganic Salt A gel sheet layer having a film thickness of 0.9 mm, containing 0.1 wt % of sodium chloride as an inorganic salt, 1 wt % of citric acid as an acid, and 28 wt % of water relative to the total weight of the gel sheet layer, was obtained in the same manner as in Reference Production Example 1, except that the amount of sodium chloride in the liquid monomer mixture was changed to 0.1 parts by weight and the thickness of the formwork of silicone rubber sheet was changed to 0.9 mm in Reference Production Example 1.

Reference Production Example 13: Production of Gel Sheet Layer Containing a Small Amount of Inorganic Salt A gel sheet layer having a film thickness of 0.9 mm, containing 0.1 wt % of sodium chloride as an inorganic salt, 0.2 wt % of citric acid as an acid, and 28 wt % of water relative to the total weight of the gel sheet layer, was obtained in the same manner as in Reference Production Example 1, except that the amount of sodium chloride was changed to 0.1 parts by weight and the amount of citric acid to 0.2 parts by weight in the liquid monomer mixture, and the thickness of the formwork of silicone rubber sheet was changed to 0.9 mm in Reference Production Example 1.

Reference Production Example 14: Production of Gel Sheet Layer not Containing Inorganic Salt A gel sheet layer having a film thickness of 0.9 mm, containing 1 wt % O/of citric acid as an acid and 28 wt % of water, not containing sodium chloride as an inorganic salt, relative to the total weight of the gel sheet layer, was obtained in the same manner as in Reference Production Example 1, except that the amount of sodium chloride in the liquid monomer mixture was changed to 0 part by weight and the thickness of the formwork of silicone rubber sheet was changed to 0.9 mm in Reference Production Example 1.

Reference Production Example 15: Production of Gel Sheet Layer not Containing Inorganic Salt A gel sheet layer having a film thickness of 0.6 mm, containing 1 wt % of citric acid as an acid and 28 wt % of water, not containing sodium chloride as an inorganic salt relative to the total weight of the gel sheet layer, was obtained in the same manner as in Reference Production Example 1, except that the amount of sodium chloride was changed to 0 part by weight and the amount of polyacrylic acid (JURYMER AC-10P, manufactured by Toagosei Co., Ltd., molecular weight: 9,000) to 1 part by weight in the liquid monomer mixture, and the thickness of the formwork of silicone rubber sheet was changed to 0.6 mm in Reference Production Example 1.

Reference Production Example 16: Production of Gel Sheet Layer not Containing Inorganic Salt A gel sheet layer having a film thickness of 0.6 mm, containing 28 wt % of water relative to the total weight of the gel sheet layer, not containing any one of sodium chloride as an inorganic salt and citric acid as an acid, was obtained in the same manner as in Reference Production Example 1, except that the amount of sodium chloride was changed to 0 part by weight, the amount of citric acid to 0 part by weight in the liquid monomer mixture, and the thickness of the formwork of silicone rubber sheet was changed to 0.6 mm in Reference Production Example 1.

<II. Production of Gel Sheet Comprising a Plurality of Gel Sheet Layers Stacked>

Reference Example 1

The gel sheet layer prepared in Reference Production Example 1, having a film thickness of 0.3 mm, containing a large amount of inorganic salt, and the gel sheet layer prepared in Reference Production Example 2, having a film thickness of 0.6 mm, not containing inorganic salt were stacked, so that a gel sheet having a total film thickness of 0.9 mm was obtained. In the gel sheet thus obtained, the gel sheet layer containing a large amount of inorganic salt corresponds to a gel sheet layer A, and the gel sheet layer not containing inorganic salt corresponds to a gel sheet layer B, respectively. In the present Reference Example, the gel sheet layer A is disposed on the top face of the gel sheet layer B.

Reference Example 2

A gel sheet having a total film thickness of 1.2 mm was obtained in the same manner as in Reference Example 1, except that the gel sheet layer B was replaced with the gel sheet layer prepared in Reference Production Example 3, having a film thickness of 0.9 mm, not containing inorganic salt, in Reference Example 1.

Reference Example 3

Two of the gel sheet layers prepared in Reference Production Example 1, having a film thickness of 0.3 mm, containing a large amount of inorganic salt, and two of the gel sheet layers prepared in Reference Production Example 2, having a film thickness of 0.6 mm, not containing inorganic salt were alternately stacked, so that a gel sheet having a total film thickness of 1.8 mm was obtained. In the gel sheet thus obtained, the two gel sheet layers containing a large amount of inorganic salt correspond to gel sheet layers A (hereinafter also referred to as "gel sheet layer A" and "gel sheet layer A'"), and the two gel sheet layers not containing inorganic salt correspond to gel sheet layers B (hereinafter also referred to as "gel sheet layer B" and "gel sheet layer B'"), respectively. In the present Example, on the top face of the gel sheet layer B, the gel sheet layer A is disposed; on the top face of the gel sheet layer A, the gel sheet layer B' is disposed; and on the top face of the gel sheet layer B', the gel sheet layer A' is disposed.

Reference Example 41

A gel sheet having a total film thickness of 1.2 mm was obtained in the same manner as in Reference Example 1, except that the gel sheet layer A was replaced with the gel sheet layer prepared in Reference Production Example 5, having a film thickness of 0.6 mm, containing a large amount of inorganic salt, and the gel sheet layer B was replaced with the gel sheet layer prepared in Reference Production Example 9, having a film thickness of 0.6 mm, containing a small amount of inorganic salt, in Reference Example 1.

Reference Example 5

A gel sheet having a total film thickness of 2.4 mm was obtained in the same manner as in Reference Example 3, except that the gel sheet layers A and A' were replaced with the gel sheet layers prepared in Reference Production Example 5, having a film thickness of 0.6 mm, containing a large amount of inorganic salt, respectively, and the gel sheet layers B and B' were replaced with the gel sheet layers prepared in Reference Production Example 9, having a film thickness of 0.6 mm, containing a small amount of inorganic salt, respectively, in Reference Example 3.

Reference Example 6

A gel sheet having a total film thickness of 1.2 mm was obtained in the same manner as in Reference Example 1, except that the gel sheet layer A was replaced with the gel sheet layer prepared in Reference Production Example 5, having a film thickness of 0.6 mm, containing a large amount of inorganic salt, and the gel sheet layer B was replaced with the gel sheet layer prepared in Reference Production Example 10, having a film thickness of 0.6 mm, containing a small amount of inorganic salt, in Reference Example 1.

Reference Example 7

A gel sheet having a total film thickness of 1.2 mm was obtained in the same manner as in Reference Example 1, except that the gel sheet layer A was replaced with the gel sheet layer prepared in Reference Production Example 5, having a film thickness of 0.6 mm, containing a large amount of inorganic salt, and the gel sheet layer B was replaced with the gel sheet layer prepared in Reference Production Example 11, having a film thickness of 0.6 mm, containing a small amount of inorganic salt, in Reference Example 1.

Reference Example 81

A gel sheet having a total film thickness of 1.5 mm was obtained in the same manner as in Reference Example 1, except that the gel sheet layer A was replaced with the gel sheet layer prepared in Reference Production Example 5, having a film thickness of 0.6 mm, containing a large amount of inorganic salt, and the gel sheet layer B was replaced with the gel sheet layer prepared in Reference Production Example 12, having a film thickness of 0.9 mm, containing a small amount of inorganic salt, in Reference Example 1.

Reference Example 91

A gel sheet having a total film thickness of 1.5 mm was obtained in the same manner as in Reference Example 1, except that the gel sheet layer A was replaced with the gel sheet layer prepared in Reference Production Example 5, having a film thickness of 0.6 mm, containing a large amount of inorganic salt, and the gel sheet layer B was replaced with the gel sheet layer prepared in Reference Production Example 13, having a film thickness of 0.9 mm, containing a small amount of inorganic salt, in Reference Example 1.

Reference Example 10

A gel sheet having a total film thickness of 0.6 mm was obtained in the same manner as in Reference Example 1, except that the gel sheet layer B was replaced with the gel sheet layer prepared in Reference Production Example 4, having a film thickness of 0.3 mm, not containing inorganic salt, in Reference Example 1.

Reference Example 11

A gel sheet having a total film thickness of 0.9 mm was obtained in the same manner as in Reference Example 1, except that the gel sheet layer B was replaced with the gel sheet layer prepared in Reference Production Example 15, having a film thickness of 0.6 mm, not containing inorganic salt, in Reference Example 1.

Reference Comparative Example 1

A gel sheet having a total film thickness of 0.9 mm was obtained in the same manner as in Reference Example 1, except that the gel sheet layer B was replaced with the gel sheet layer prepared in Reference Production Example 5, having a film thickness of 0.6 mm, containing a large amount of inorganic salt, in Reference Example 1.

Reference Comparative Example 2

A gel sheet having a total film thickness of 1.2 mm was obtained in the same manner as in Reference Example 1, except that the gel sheet layer B was replaced with the gel sheet layer prepared in Reference Production Example 6, having a film thickness of 0.9 mm, containing a large amount of inorganic salt, in Reference Example 1.

Reference Comparative Example 3

A gel sheet having a total film thickness of 1.5 mm was obtained in the same manner as in Reference Example 1, except that the gel sheet layer A was replaced with the gel sheet layer prepared in Reference Production Example 5, having a film thickness of 0.6 mm, containing a large amount of inorganic salt, and the gel sheet layer B was replaced with the gel sheet layer prepared in Reference Production Example 6, having a film thickness of 0.9 mm, containing a large amount of inorganic salt, respectively, in Reference Example 1.

Reference Comparative Example 4

A gel sheet having a total film thickness of 0.9 mm was obtained in the same manner as in Reference Example 1, except that the gel sheet layer A was replaced with the gel sheet layer prepared in Reference Production Example 4, having a film thickness of 0.3 mm, not containing inorganic salt, and the gel sheet layer B was replaced with the gel sheet layer prepared in Reference Production Example 2, having a film thickness of 0.6 mm, not containing inorganic salt, respectively, in Reference Example 1.

Reference Comparative Example 5

A gel sheet having a total film thickness of 1.2 mm was obtained in the same manner as in Reference Example 1, except that the gel sheet layer A was replaced with the gel sheet layer prepared in Reference Production Example 4, having a film thickness of 0.3 mm, not containing inorganic salt, and the gel sheet layer B was replaced with the gel sheet layer prepared in Reference Production Example 3, having a film thickness of 0.9 mm, not containing inorganic salt, respectively, in Reference Example 1.

Reference Comparative Example 6

A gel sheet having a total film thickness of 1.5 mm was obtained in the same manner as in Reference Example 1, except that the gel sheet layer A was replaced with the gel sheet layer prepared in Reference Production Example 2, having a film thickness of 0.6 mm, not containing inorganic salt, and the gel sheet layer B was replaced with the gel sheet layer prepared in Reference Production Example 3, having a film thickness of 0.9 mm, not containing inorganic salt, respectively, in Reference Example 1.

Reference Comparative Example 7

A gel sheet having a total film thickness of 0.9 mm was obtained in the same manner as in Reference Example 1, except that the gel sheet layer B was replaced with the gel sheet layer prepared in Reference Production Example 16, having a film thickness of 0.6 mm, not containing inorganic salt, in Reference Example 1.

Reference Comparative Example 8

A gel sheet having a total film thickness of 0.9 mm was obtained in the same manner as in Reference Example 1, except that the gel sheet layer A was replaced with the gel sheet layer prepared in Reference Production Example 7, having a film thickness of 0.3 mm, containing a large amount of inorganic salt, and the gel sheet layer B was replaced with the gel sheet layer prepared in Reference Production Example 8, having a film thickness of 0.6 mm, containing a large amount of inorganic salt, respectively, in Reference Example 1.

Reference Comparative Example 9

A gel sheet having a total film thickness of 0.9 mm was obtained in the same manner as in Reference Example 1, except that the gel sheet layer A was replaced with the gel sheet layer prepared in Reference Production Example 2, having a film thickness of 0.6 mm, not containing inorganic salt, and the gel sheet layer B was replaced with the gel sheet layer prepared in Reference Production Example 1, having a film thickness of 0.3 mm, containing a large amount of inorganic salt, respectively, in Reference Example 1.

<III: Evaluation of Gel Sheet>
[III-1: Change in Resistance Value for Direct Current Application>

Two sets each of the test materials of gel sheet in Reference Examples or Reference Comparative Examples cut into 25-mm squares, held between two SUS plates, respectively, were prepared. To the SUS plate adjacent to the gel sheet layer A (Reference Examples 1, 2, 4 and 6 to 11, and Reference Comparative Examples 1 to 9) or the gel sheet layer A' (Reference Examples 3 and 5) of one of the test materials of the two sets, the positive electrode of a stabilized DC power supply (PAR 18-6A, manufactured by TEXIO) was connected, and to the SUS plate adjacent to the gel sheet layer B of the other test material, the negative electrode was connected, respectively. Of the two sets of the test materials, between one SUS plate adjacent to the gel sheet layer B not connected to any of the positive electrode or the negative electrode and another SUS plate adjacent to the gel sheet layer A (Reference Examples 1, 2, 4 and 6 to 11, and Reference Comparative Examples 1 to 9) or the gel sheet layer A' (Reference Examples 3 and 5), a resistance of 1 kΩ was connected. In the circuit, the resistance simulates the surface of an adherend such as the skin of a living body. To the circuit, a direct current was applied under application conditions with an applied DC voltage of 3V for an application time of 10 minutes. Based on the measured resistance of the circuit, the test material with no change in resistance was rated as good, and the test material with increased resistance was rated as poor.

[III-2: Change in pH for Direct Current Application]

In the same manner as described in III-1, a direct current was applied to a circuit connected to each of the test materials of gel sheets in Reference Examples and Reference Comparative Examples. After the application, the gel sheet was removed from the test material. A pH test paper was placed on the surface of the gel sheet layer B of each of the gel sheets in Reference Examples and Reference Comparative Examples. Both of the surfaces of the gel sheet were held between PET films to keep for 1 minute. The pH test paper was then taken out to confirm the pH value. The pH value of the gel sheet layer B of each of the gel sheet in Reference Examples and Reference Comparative Examples before application of the direct current was measured in the same manner. As a result, any of the gel sheets in Reference Examples and Reference Comparative Examples had a pH of 5. Based on the pH before application of the direct current, the gel sheet with a pH value after application in the range of 3 to 8 was rated as good, and in the range of 2 or less, or 9 or more as poor.

[III-3: Evaluation Results]

Of the gel sheets in Reference Examples and Reference Comparative Examples each, the dimensions and the amount of inorganic salt of the gel sheet layer, and the evaluation results with direct current applied to the gel sheet are shown in Table 3.

TABLE 3

| | | Gel sheet layer A | | Gel sheet layer B | | | | | Gel sheet layer A' | |
|---|---|---|---|---|---|---|---|---|---|---|
| | | Thickness a [mm] | Salt concentration X [wt %] | Thickness b [mm] | Salt concentration Y [wt %] | Amount of acid [wt %] | Water content α [wt %] | Y/α | Thickness a' [mm] | Salt concentration X' [wt %] |
| Reference Example | 1 | 0.3 | 5 | 0.6 | 0 | 1 | 28 | 0 | — | — |
| | 2 | 0.3 | 5 | 0.9 | 0 | 1 | 28 | 0 | — | — |
| | 3 | 0.3 | 5 | 0.6 | 0 | 1 | 28 | 0 | 0.3 | 5 |
| | 4 | 0.6 | 5 | 0.6 | 0.1 | 1 | 23 | 0.004 | — | — |
| | 5 | 0.6 | 5 | 0.6 | 0.1 | 1 | 28 | 0.004 | 0.6 | 5 |
| | 6 | 0.6 | 5 | 0.6 | 0.1 | 1 | 38 | 0.003 | — | — |
| | 7 | 0.6 | 5 | 0.6 | 0.5 | 1 | 50 | 0.010 | — | — |
| | 8 | 0.6 | 5 | 0.9 | 0.1 | 1 | 28 | 0.004 | — | — |
| | 9 | 0.6 | 5 | 0.9 | 0.1 | 0.2 | 28 | 0.004 | — | — |
| | 10 | 0.3 | 5 | 0.3 | 0 | 1 | 28 | 0 | — | — |
| | 11 | 0.3 | 5 | 0.6 | 0 | 1 | 28 | 0 | — | — |
| Reference Comparative Example | 1 | 0.3 | 5 | 0.6 | 5 | 1 | 28 | 0.179 | — | — |
| | 2 | 0.3 | 5 | 0.9 | 5 | 1 | 28 | 0.179 | — | — |
| | 3 | 0.6 | 5 | 0.9 | 5 | 1 | 28 | 0.179 | — | — |
| | 4 | 0.3 | 0 | 0.6 | 0 | 1 | 28 | 0 | — | — |
| | 5 | 0.3 | 0 | 0.9 | 0 | 1 | 28 | 0 | — | — |
| | 6 | 0.6 | 0 | 0.9 | 0 | 1 | 28 | 0 | — | — |
| | 7 | 0.3 | 5 | 0.6 | 0 | 0 | 28 | 0 | — | — |
| | 8 | 0.3 | 2.5 | 0.6 | 2.5 | 1 | 28 | 0.089 | — | — |
| | 9 | 0.6 | 0 | 0.3 | 5 | 1 | 28 | 0.179 | — | — |

| | | Gel sheet layer B' | | | | | Gel sheet Thickness [mm] | Resistance Rating | pH of layer B after application | |
|---|---|---|---|---|---|---|---|---|---|---|
| | | Thickness b' [mm] | Salt concentration Y' [wt %] | Amount of acid [wt %] | Water content α' [wt %] | Y/α' | | | pH | Rating |
| Reference Example | 1 | — | — | — | — | — | 0.9 | Good | 6 | Good |
| | 2 | — | — | — | — | — | 1.2 | Good | 5 | Good |
| | 3 | 0.6 | 0 | 1 | 26 | 0 | 1.8 | Good | 5 | Good |
| | 4 | — | — | — | — | — | 1.2 | Good | 6 | Good |
| | 5 | 0.6 | 0.1 | 1 | 28 | 0.004 | 2.4 | Good | 5 | Good |
| | 6 | — | — | — | — | — | 1.2 | Good | 5 | Good |
| | 7 | — | — | — | — | — | 1.2 | Good | 5 | Good |
| | 8 | — | — | — | — | — | 1.5 | Good | 5 | Good |
| | 9 | — | — | — | — | — | 1.5 | Good | 7 | Good |
| | 10 | — | — | — | — | — | 0.6 | Good | 8 | Good |
| | 11 | — | — | — | — | — | 0.9 | Good | 6 | Good |
| Reference Comparative Example | 1 | — | — | — | — | — | 0.9 | Good | 9 | Poor |
| | 2 | — | — | — | — | — | 1.2 | Good | 9 | Poor |
| | 3 | — | — | — | — | — | 1.5 | Good | 9 | Poor |
| | 4 | — | — | — | — | — | 0.9 | Poor | 5 | Good |
| | 5 | — | — | — | — | — | 1.2 | Poor | 5 | Good |
| | 6 | — | — | — | — | — | 1.5 | Poor | 5 | Good |
| | 7 | — | — | — | — | — | 0.9 | Good | 9 | Poor |
| | 8 | — | — | — | — | — | 0.9 | Good | 9 | Poor |
| | 9 | — | — | — | — | — | 0.9 | Good | 9 | Poor |

As shown in Table 3, each of the gel sheets in Reference Examples 1 to 11 had no change in the resistance value, with a pH value of the gel sheet layer B unchanged or in the range of 5 to 8, after application of direct current under the conditions described above. In contrast, each of the gel sheets in Reference Comparative Examples 1 to 3 and 7 to 9 had no change in the resistance value, but the pH value of the gel sheet layer B increased to 9, after application of direct current under the conditions described above. Also, each of the gel sheets in Reference Comparative Examples 4 to 6 had an increased resistance value, though the gel sheet layer B had no change in the pH value, after application of direct current under the conditions described above.

The change in pH of the gel sheets in Reference Examples 3 and 5 was evaluated in the same manner as described above after 7 days from the preparation of the gel sheets, and it was found that pH was maintained at 5. From the results, it was proved that the gel sheet comprising four gel sheet layers suppresses the material transfer between the gel sheet layers, enabling the effect of the present invention to be exhibited for a longer period.

REFERENCE SIGNS LIST

1: Gel sheet
101: Gel sheet
10: Gel material
11, 11a, 11b and 11c: Gel sheet layer A
12, 12a, 12b and 12c: Gel sheet layer B
20: Intermediate base
13, 13a, 13b, 13c, 13ab and 13bc: Membrane
14: Supporting base
21: Electrode
301: Electrode pad
T: Thickness of gel sheet
S: Amplitude of intermediate base
P: Surface of adherend All the publications, patents and patent applications cited in the present specification is directly incorporated in the present specification by citation.

The invention claimed is:

1. A gel sheet comprising a gel material and an intermediate base embedded in the gel material, and satisfying the following expression (1):

$$S/T \leq 0.4 \quad (1)$$

wherein T represents a thickness of the gel sheet, and S represents an amplitude of the intermediate base, wherein the gel material comprises at least two gel sheet layers having a gel sheet layer A and a gel sheet layer B alternately stacked, wherein the gel sheet layer A comprises at least one inorganic salt at a total content of X wt % relative to the total weight of the gel sheet layer A; and the gel sheet layer B comprises at least one inorganic salt at a total content of Y wt % relative to the total weight of the gel sheet layer B, wherein Y is less than X; and the gel sheet layer B comprises at least one acid.

2. The gel sheet according to claim 1, wherein the at least one acid comprises an organic acid.

3. The gel sheet according to claim 1, wherein X and Y satisfy the following expression (3):

$$0 \leq Y < X \leq 15 \quad (3).$$

4. The gel sheet according to claim 1, wherein when the gel sheet layer B has a water content of a wt % relative to the total weight of the gel sheet layer B, Y and α satisfy the following expression (4):

$$0 \leq Y/\alpha \leq 0.03 \quad (4).$$

5. The gel sheet according to claim 1, wherein when the gel sheet layer A has a thickness of a (mm), and the gel sheet layer B has a thickness of b (mm), a and b satisfy the following expressions (5) and (6):

$$b/a \geq 1 \quad (5)$$

$$0.6 \leq a+b \leq 3.0 \quad (6).$$

6. An electrode pad comprising the gel sheet according to claim 1 and an electrode electrically connected to the gel sheet layer A or the gel sheet layer B of the gel sheet.

7. An electrode pad for use on a living body, comprising the gel sheet according to claim 1 and an electrode electrically connected to the gel sheet layer A or the gel sheet layer B of the gel sheet, wherein the gel sheet layer A or the gel sheet layer B not connected to the electrode of the gel sheet is used as a part in contact with a living body.

8. An electrotherapeutic equipment for use on a living body, comprising the electrode pad for use on a living body according to claim 7 and a power supply part electrically connected to the electrode of the electrode pad for use on a living body, wherein the gel sheet layer A of the electrode pad for use on a living body is disposed adjacent to the positive electrode, and the gel sheet layer B is disposed adjacent to the negative electrode.

9. The electrotherapeutic equipment for use on a living body according to claim 8, for application of direct current.

10. The electrode pad for use on a living body according to claim 7, for application of direct current.

* * * * *